United States Patent [19]

Mitchell et al.

[11] Patent Number: 5,072,687
[45] Date of Patent: Dec. 17, 1991

[54] ABSORBENT PRODUCT FOR PERSONAL USE

[75] Inventors: Winalee G. Mitchell; James Mitchell, both of 110 Secor Woods La., Perrysburg, Ohio 43551; Michael Plotka, Waterville, Ohio; Gary Van Streader, Bowling Green; Thomas Krassow, North Baltimore, both of Ohio

[73] Assignees: James G. Mitchell; Winalee G. Mitchell, both of Perrysburg, Ohio

[21] Appl. No.: 566,254

[22] Filed: Aug. 13, 1990

Related U.S. Application Data

[63] Continuation-in-part of Ser. No. 372,030, Jun. 27, 1990, which is a continuation-in-part of Ser. No. 352,491, May 16, 1989, abandoned, which is a continuation-in-part of Ser. No. 272,160, Nov. 16, 1988, abandoned.

[51] Int. Cl.$^5$ .................. B05B 3/02; B05C 11/00
[52] U.S. Cl. .................. 118/37; 118/72; 118/308; 118/325; 222/368
[58] Field of Search .................. 118/37, 72, 212, 308, 118/325; 222/414, 345, 368; 604/367, 383

[56] References Cited

U.S. PATENT DOCUMENTS

| | | | |
|---|---|---|---|
| 3,387,751 | 6/1968 | Olsson | 222/267 |
| 3,620,423 | 11/1971 | Dalgleish | 222/414 |
| 3,730,397 | 5/1973 | Magnus | 222/254 |
| 4,053,088 | 10/1977 | Grataloup | 222/312 |
| 4,611,555 | 9/1986 | Burford | 118/684 |
| 4,626,184 | 12/1986 | Hammond | 425/83.1 |
| 4,655,161 | 4/1987 | Thompson | 118/24 |
| 4,715,315 | 12/1987 | Burford | 222/368 |
| 4,788,932 | 12/1988 | Kullman et al. | 118/211 |
| 4,800,102 | 1/1989 | Takada | 427/197 |
| 4,927,346 | 5/1990 | Kaiser et al. | 425/81.1 |

Primary Examiner—Richard V. Fisher
Assistant Examiner—Charles K. Friedman
Attorney, Agent, or Firm—David C. Purdue; John C. Purdue

[57] ABSTRACT

Several embodiments of apparatus for producing disposable absorbent personal articles are disclosed. According to one embodiment, apparatus is disclosed for depositing superabsorbent polymer powder on a portion of a fluff mat in a given concentration greater than zero and a second, different concentration of superabsorbent polymer powder on another portion of a fluff layer, so that there is a heavier concentration of super absorbent polymer in a target area than in areas adjacent the target area. Such apparatus has a dosing cylinder with a discontinuous outer cylindrical surface which has a pattern of first dosing depressions adjacent to a pattern of second dosing depressions. The dosing cylinder is rotated through a polymer powder hopper and powder received in the first and second depressions is sequentially discharged from the hopper and deposited on a fluff substrate in alternating areas of high powder concentration and low powder concentration. Discreet sections of the fluff containing superabsorbent are cut and incorporated in personal absorbent articles and apparatus for marking such articles is disclosed so that the mark gives an indica..on as to whether or not the apparatus is operating synchronously or not.

8 Claims, 15 Drawing Sheets

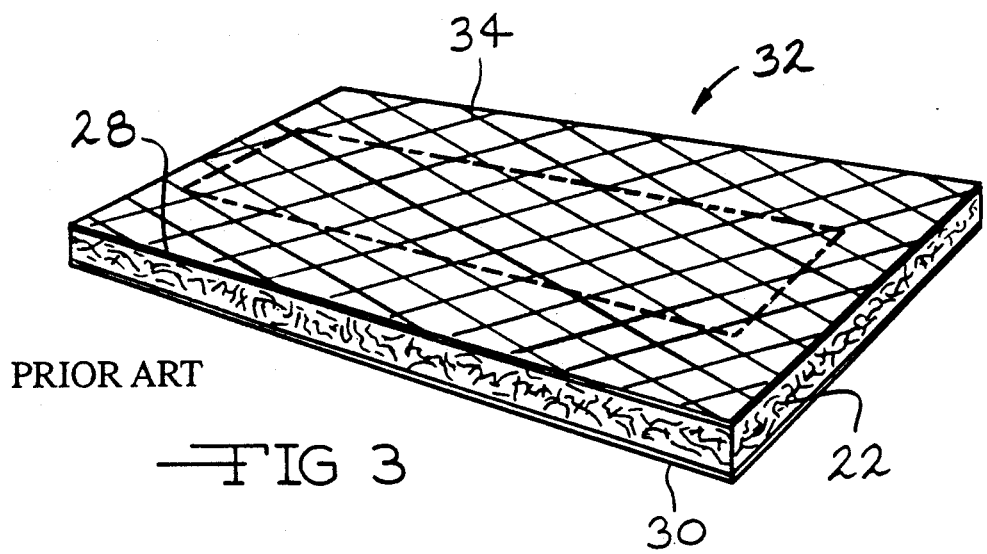
PRIOR ART
FIG 3
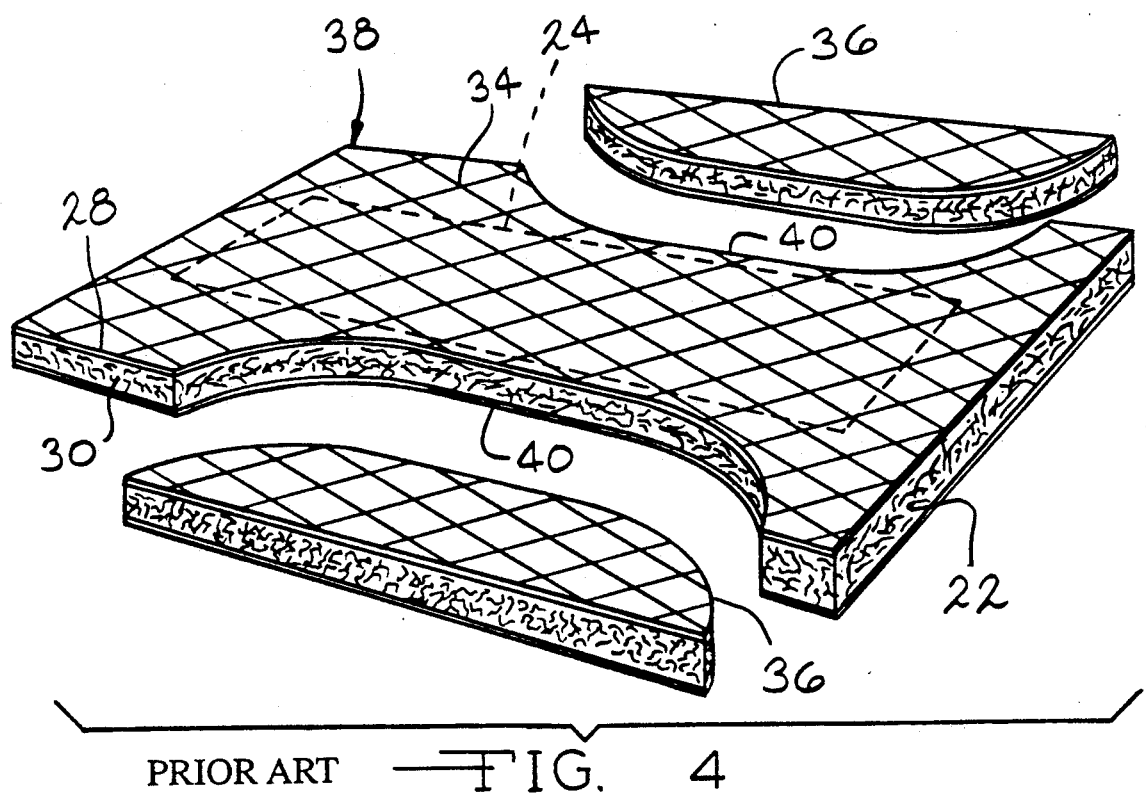
PRIOR ART FIG. 4

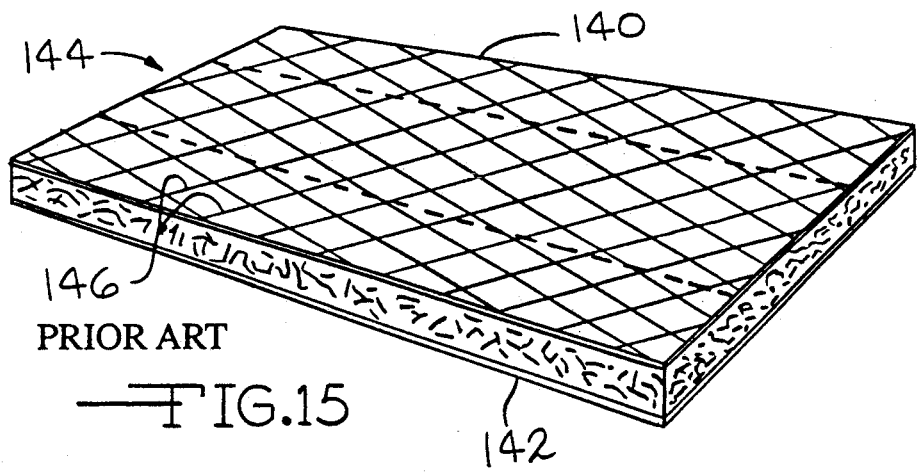
PRIOR ART
FIG. 15
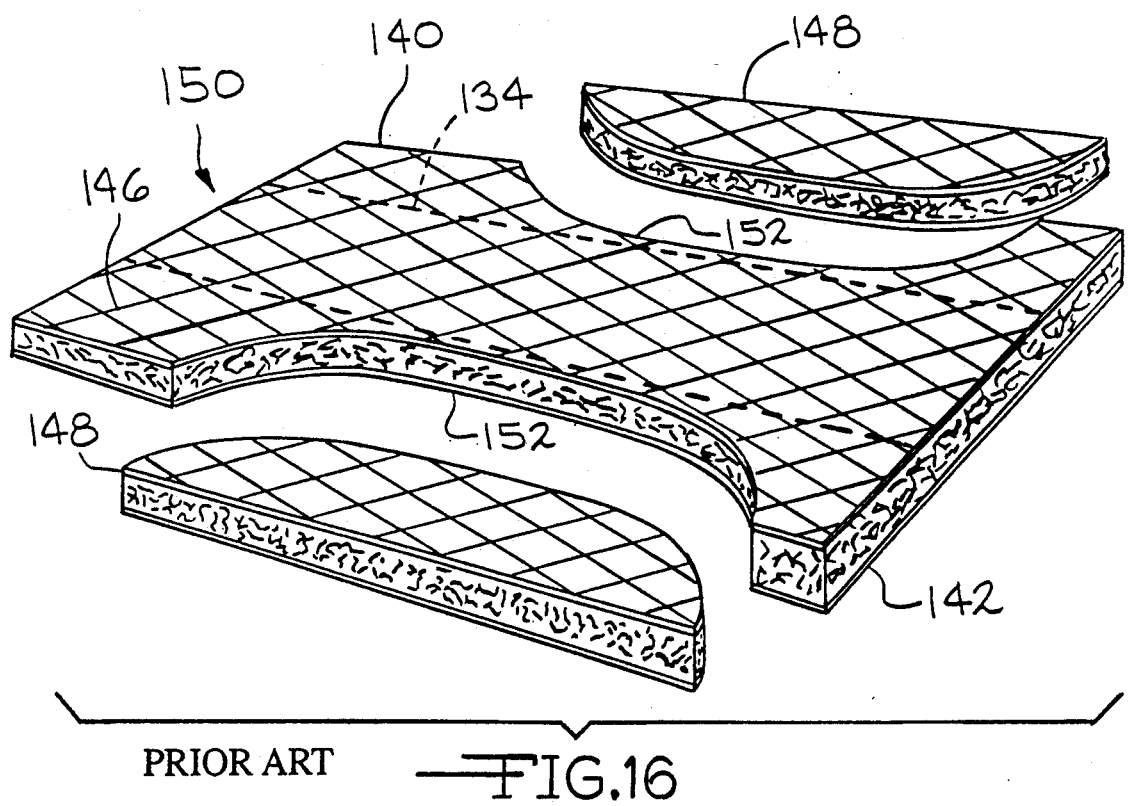
PRIOR ART   FIG. 16

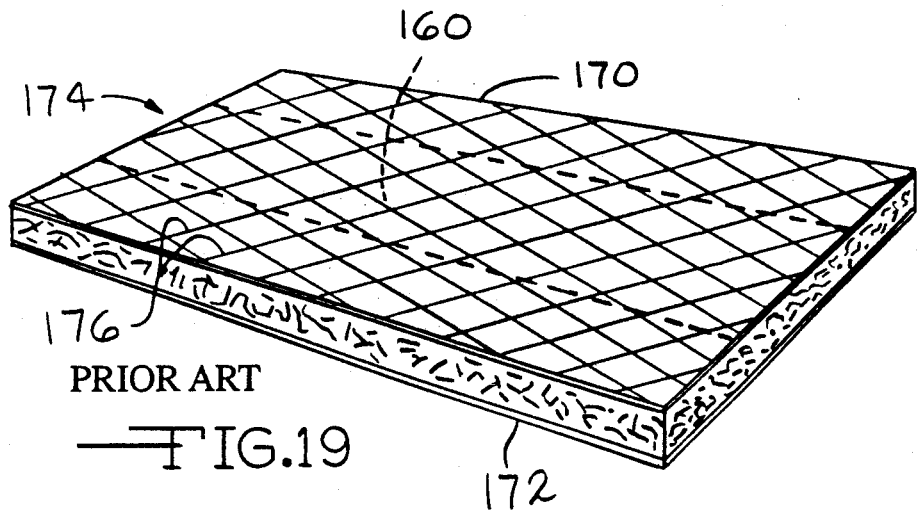
PRIOR ART
FIG. 19
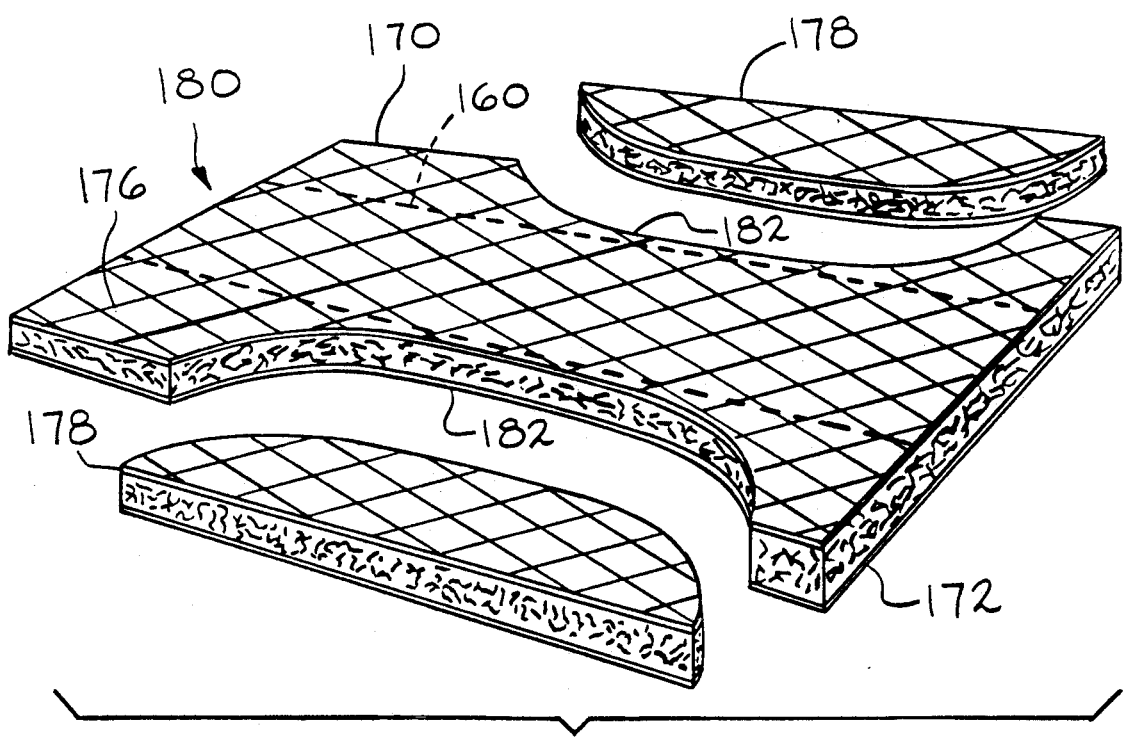
PRIOR ART FIG. 20

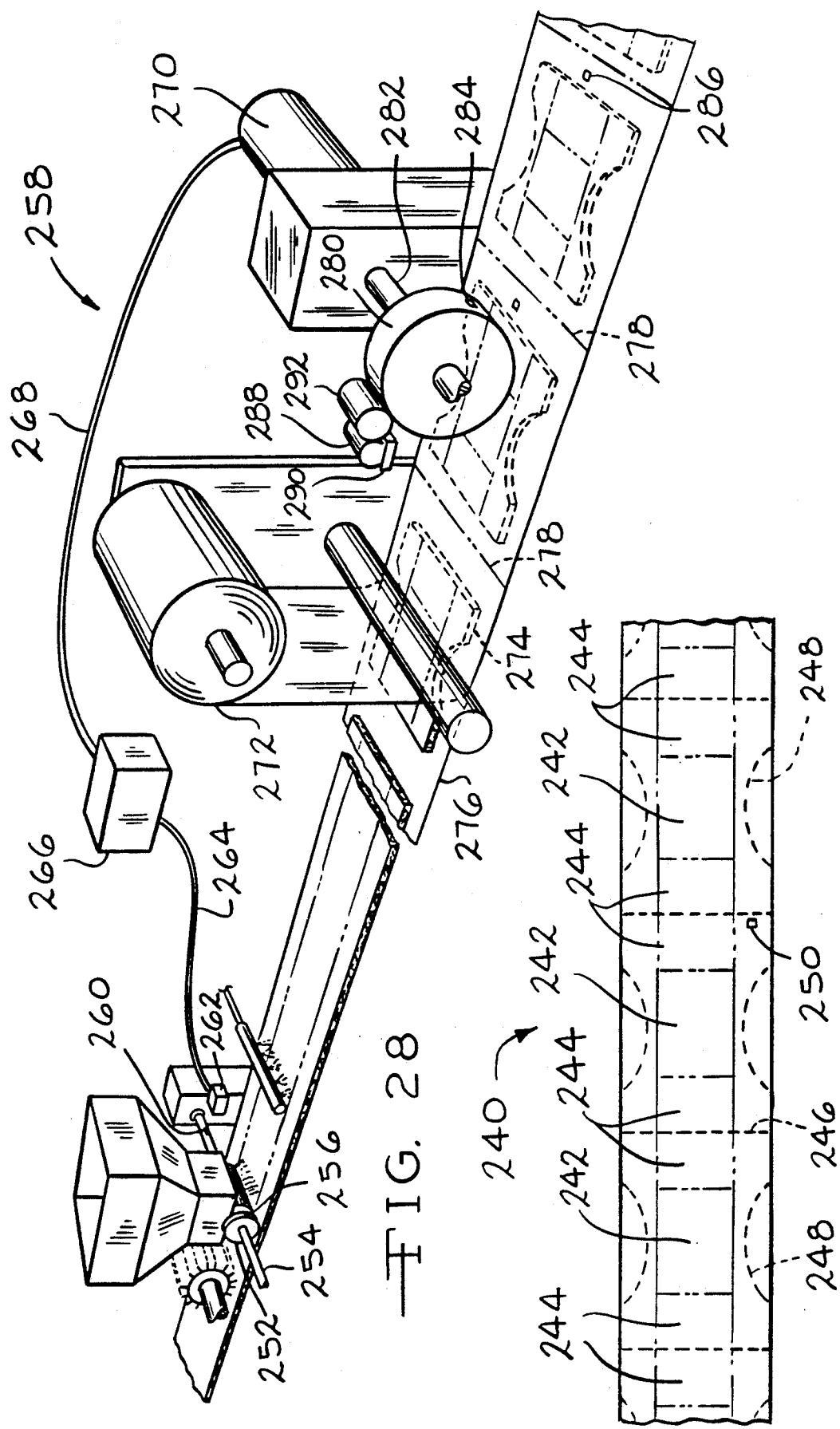

ABSORBENT PRODUCT FOR PERSONAL USE

REFERENCE TO RELATED APPLICATION

This is a continuation-in-part of application Ser. No. 07/372,030, filed June 27, 1990 which was, in turn, a continuation-in-part of application Ser. No. 352,491 filed May 16, 1989, now abandoned, itself a continuation-in-part of application Ser. No. 272,160 filed Nov. 16, 1988, now abandoned.

BACKGROUND OF THE INVENTION

1. Field of the Invention.

This invention relates to the field of absorbent products, especially for use by persons with incontinence. Specifically, the invention is concerned with diapers or underpants type products, as well as absorbent pads and the like, which are highly absorptive due to the inclusion of a super absorbent polymer in an embossed target area.

2. Description of the Prior Art

There has been a great deal of recent development in the field of personal absorbent products ranging from diapers for infants to adult briefs for people with urinary incontinence. One major area of development has been broadly in the field of super absorbent polymers, such as starches, acrylics, modified cellulose, gums and the like. In some respects, the super absorbent polymers are far superior to cellulose fluff and other conventional absorbent media used in personal absorbent products. For example, the polymers, on a weight basis, have an absorption capacity which is far greater than fluff. In addition, super absorbent polymers retain absorbed liquid, even under pressure, far better than fluff which is subject to "squeeze-out" where absorbed liquid is released from fluff when it is subjected to pressure.

There are some drawbacks, however, to super absorbent polymers used as components of personal absorbent products. Generally, super absorbent polymers are inferior to fluff in terms of rate of absorption of liquid. Another drawback of super absorbent polymers is their susceptibility to what is referred to as "gel-blocking" where a layer containing super absorbent polymer is wetted, the polymer absorbs the liquid and the gelled polymer, which has expanded to many times its dry size, blocks additional liquid from passing through the layer. Super absorbent polymers, because they are finely powdered, present manufacturing difficulties in terms of satisfactory incorporation of the powder into absorbent products. One problem with the superabsorbent polymer powder is migration of the powder from its original position within the product, before the product is wetted.

In the field of apparatus for depositing superabsorbent polymer powder, U.S. Pat. Nos. 4,800,102 and 4,927,346, commonly assigned to Nordson Corporation, disclose two approaches to the task of intermittently depositing polymer onto fluff in discreet areas. U.S. Pat. No. 4,800,102 discloses apparatus including an apertured disc which is rotated about a vertical axis and polymer powder is deposited on the disc from which it is scraped so that it falls through the apertures and onto a fluff layer. U.S. Pat. No. 4,927,346 discloses vacuum deposition apparatus for intermittently depositing polymer powder on a fluff substrate.

Super absorbent polymers have been incorporated into absorbent products in a variety of ways. In some cases, super absorbent polymer is sprinkled into a fluff layer or deposited between two fluff layers, as disclosed in U.S. Pat. No. 4,381,782, but these approaches are plagued by problems arising from the migration of the powder from the place it is deposited. Another approach entails the use of tissue with super absorbent polymer powder fixed to it. Such tissue, also known as laminate, has been used in absorbent products alone and in combination with conventional fluff.

Examples of the use of laminate alone are shown in U.S. Pat. No. 4,568,341. This patent discloses a special laminate structure including undulations and small hinge and flap members formed in the laminate. This laminate structure compensates for the relatively slow absorbency rate of the super absorbent polymer in the laminate.

Composite absorbent products including one or more layers of laminate and one or more layers of fluff are disclosed in U.S. Pat. Nos. 3,888,256, 4,333,465, 4,411,660, 4,592,751, 4,622,036, 4,643,726 and 4,699,619.

U.S. Pat. No. 4,055,180 discloses an absorbent article including super absorbent polymer powder disposed in pockets formed in an absorbent pad.

A product distributed under the trademark SLIMLINE comprises a backing sheet, a facing sheet, a layer of laminate adjacent to the facing sheet and a layer of fluff between the laminate and the backing sheet.

SUMMARY OF THE INVENTION

The instant invention is based upon the discovery of an improved absorbent article incorporating an improved absorbent insert or core and apparatus for producing them. According to a preferred embodiment of the invention, the insert comprises a fluff layer with a first target area having a given, relatively high concentration of polymer powder and at least one second area having a relatively low concentration of polymer powder. Apparatus for producing the fluff layer comprises a hopper and a dosing cylinder partially disposed in the bottom of the hopper. The dosing cylinder is rotated so that first dosing depressions and second dosing depressions are sequentially positioned within the hopper, where they fill with polymer powder, and outside of the hopper where they discharge the polymer powder.

In absorbent articles according to the invention, the fluff layer is physically integrated to at least one layer of laminate which comprises at least one layer of tissue with superabsorbent polymer secured to and supported thereon. The insert is positioned in the absorbent article so that the laminate constitutes an upper layer, i.e., it will be adjacent to a wearer, in use. In a preferred embodiment, the fluff layer and the laminate are embossed between rollers that physically integrate the two layers and produce transfer sites through which liquid is rapidly transferred through the laminate layer into the fluff layer, away from a wearer.

In another embodiment, an absorbent insert is produced by embossing a laminate between a smooth roller and a patterned roller and trimming and folding the embossed laminate. The insert is folded to produce an insert with a central region with an exposed pattern of embossed depressions and, on each side of the central region, lateral regions with an exposed, smooth surface.

In yet another embodiment, an absorbent insert is produced by depositing super absorbent polymer powder on a portion of a layer of fluff, covering the powder with at least one tissue layer, and embossing the assembly to produce an integrated absorbent insert with transfer sites through which liquid is rapidly transferred into the fluff layer, away from a wearer. In a preferred mode of this embodiment, there is a heavier concentration of superabsorbent polymer in a target area than in adjacent regions of the product. This concentration is achieved through the use of special manufacturing equipment.

According to another embodiment, an absorbent insert is produced by depositing super absorbent polymer powder on a portion of a layer of fluff, covering at least a portion of the fluff with polymer deposited thereon, with at least one laminate layer, and embossing the assembly to produce an integrated absorbent insert with transfer sites through which liquid is rapidly transferred into the fluff layer for absorption by the polymer powder dispersed in the fluff.

BRIEF DESCRIPTION OF THE DRAWINGS

FIG. 3 is a perspective view of an absorbent core comprising the components illustrated in FIG. 2, after they have been integrated by an embossing operation.

FIG. 4 is a perspective view of the absorbent core during a trimming operation.

FIG. 15 is a perspective view of an absorbent core comprising the components illustrated in FIG. 14, after they have been integrated by an embossing operation.

FIG. 16 is a perspective view of the absorbent core during a trimming operation.

FIG. 19 is a perspective view of an absorbent core comprising the components illustrated in FIG. 18, after they have been integrated by an embossing operation.

FIG. 20 is a perspective view of the absorbent core during a trimming operation.

FIG. 27 is an elevational view of a continuous fluff layer containing superabsorbent polymer which has been deposited by apparatus such as that shown in FIG. 21.

FIG. 28 is a perspective view of apparatus similar to that illustrated in FIG. 21 but further including means for providing a visually perceptible mark indicative of whether or not the apparatus is functioning synchronously.

DETAILED DESCRIPTION OF THE INVENTION

Figure 1:
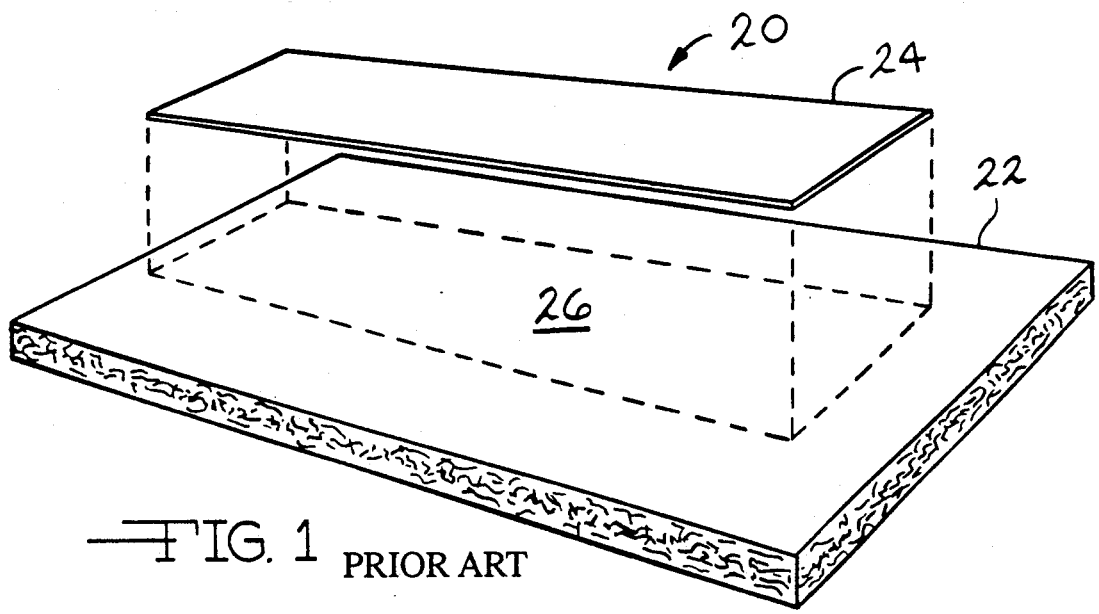
FIG. 1 is an exploded, perspective view of the absorptive components of one embodiment of an absorbent product according to the present invention.

Referring now to FIG. 1, absorptive components of one embodiment of an absorptive product are indicated generally at 20. One of the absorptive components 20 is a relatively thick, fluff layer of moisture absorbing material 22, such as cellulose fluff, fluffed wood pulp, batting or the like. The other one of the absorptive components 20 is a layer of laminate 24 comprising tissue with particles of a super absorbent polymer deposited thereon and secured thereto. A preferred material for the laminate layer 24 is a laminate containing a super absorbent polymer of the modified acrylic type. Such a laminate is available from Gelok International under the trademark "Gelok 6000 double ply/double ply (1080)".

The laminate layer 24 is superposed on a central target area 26 of the fluff layer 22, as indicated by dotted lines in FIG. 1. The laminate layer 24 does not extend the full length or width of the fluff layer 22, although a larger laminate layer may be used. The laminate layer 24 has an extremely high absorption capacity but the laminate itself is relatively expensive. Accordingly, the laminate layer is advantageously restricted to the target area 26 which coincides with the area where urine voided by a wearer will first contact the absorptive product. In the target area 26, the need for absorptive capacity is the greatest and the laminate layer 24 meets this need.

Before the laminate layer 24 is deposited on the fluff layer 22, water is sprayed on the central region 26 of the fluff layer 22. The moisture serves to adhere the laminate layer 24 to the fluff layer 22 during subsequent assembly operations. The amount of water to be sprayed is not critical, but there should be enough water to provide some modicum of adhesion between the layers 22 and 24. On the other hand, the amount of water should be only enough to moisten the upper surface of the fluff layer 22.

Figure 2:
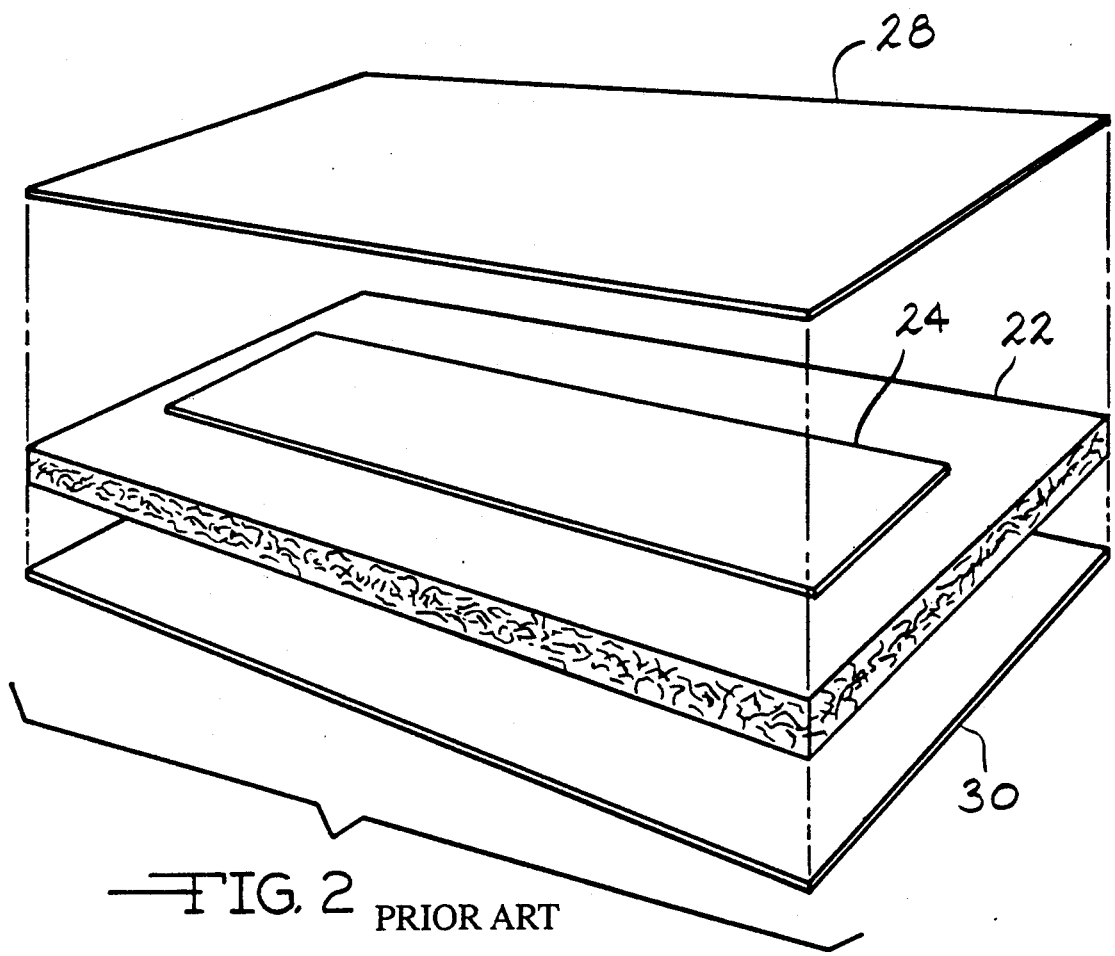
FIG. 2 is an exploded, perspective view of the absorptive components illustrated in FIG. 1, and upper and lower tissue layers.

After water has been sprayed on the fluff layer 22, the laminate layer 24 is deposited on the fluff layer 22 in the target area 26, as shown in FIG. 2. An upper layer of tissue 28 is positioned on top of the layers 22 and 24 while a lower layer of tissue 30 is positioned below the layer 22. After the tissue layers 28 and 30 are brought into contact with the absorbent core 20, the components are subjected to an embossing step. A smooth roller (not shown) is applied to the lower tissue layer 30 and a patterned roller (not shown) is applied to the opposed, upper tissue layer 28 to produce an embossed absorbent core 32. A suitable diamond embossing pattern is shown in FIG. 3, reflected in the pattern shown on the surface of the tissue layer 30. The embossing pattern on the embossing die (not shown) applied to the upper tissue layer 28 produces a pattern of channels 34 in the surface of the tissue layer 28, in the laminate layer 24, and in the fluff layer 22. As is explained below, these channels 34 constitute transfer sites through which liquid is absorbed quickly from above the upper tissue layer 28, through the laminate layer 24, to the fluff layer where it will be absorbed. The channels 34 are interconnected in a continuous network which promotes excellent wicking characteristics.

In the channels 34, there is a high density interface between the tissue layer 28, the laminate layer 24 and the fluff layer 22. In this interface, there is a physical bond between the layers 28, 24 and 22 which gives the absorbent core 32 physical integrity. In the areas between the channels 34, the layers 28, 24 and 22 have a lower density than these layers have in the channels 34.

The embossing step can be carried out advantageously with approximately 50 to 175 lbs of pressure per lineal inch of the embossing rollers. A variety of patterns would be suitable for the patterned embossing roller, beside the one reflected in the upper tissue layer 28 shown in FIG. 3. Particulars about the embossing pattern are discussed below in connection with some examples of the invention.

The embossing operation was carried out with and without the step of spraying water on the fluff layer. In the cases where no water was sprayed, the embossing step did not result in a physical bond between the fluff layer and the laminate layer. Rather, the laminate layer and the fluff layer remained discreet layers, like the layers in the prior art Slimline product. However, when the embossing operation was carried out after water had been sprayed on the fluff layer, a physical bond was produced between the fluff layer and the laminate layer.

It will be appreciated that the manufacturing steps described above with reference to FIGS. 1–3 can be applied to bulk materials supplied, for example, from rolls. Specifically, the fluff layer 22, the laminate layer 24 and the tissue layers 28 and 30 can be manufactured into an embossed, absorbent core 32 of infinite length which can later be cut to appropriate length and incorporated into an absorbent product according to the instant invention. After the absorbent core 32 has been embossed, it is preferably subjected to a de-bulking operation in which it is passed between two compression rollers (not shown). This step adds further integrity to the embossed absorbent core 32 and promotes more economical packaging by producing thinner absorbent products.

Referring now to FIG. 4, the embossed absorbent core 32 is illustrated after ears 36 have been trimmed therefrom to produce an absorbent insert 38, with leg cut outs 40, for incorporation in an absorbent product. The cut outs 40 extend inwardly toward, but terminate just short of, the laminate layer 24. The ears 36 can be recycled, if desired, to yield material suitable for producing additional fluff layers 22. The trimming can be carried out with a die-cutter which may include a cutter for cutting the embossed absorbent core 32 to produce an absorbent insert 38 of a given length. Alternatively, a separate cutter may be used to cut absorbent core material to an appropriate length.

Figure 5:
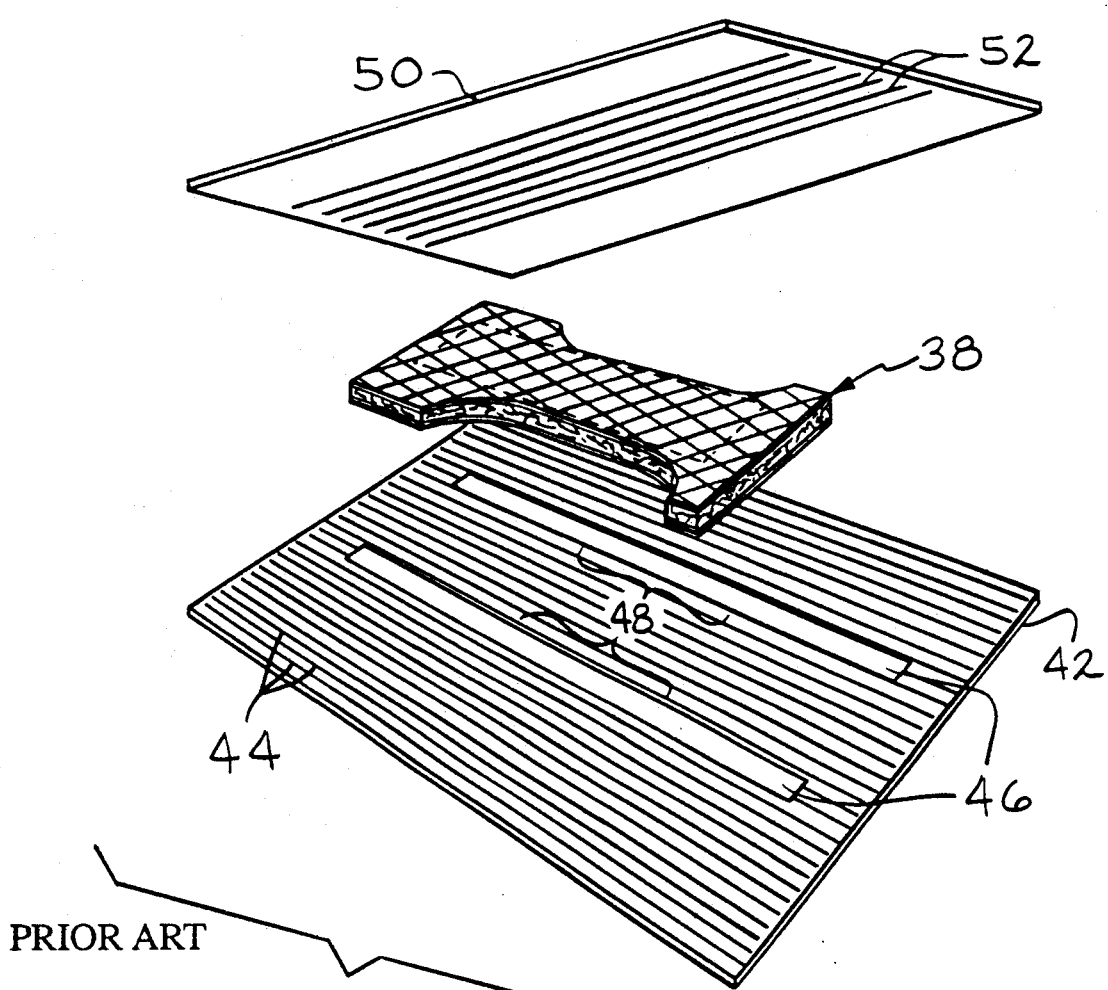
FIG. 5 is an exploded, perspective view of the components of one embodiment of an absorbent product incorporating the absorbent core illustrated in FIG. 4.

With reference to FIG. 5, a water impervious backing sheet 42 is illustrated below the absorbent insert 38. A plurality of lines 44 of a hot melt type adhesive are applied longitudinally to the backing sheet 42, across the entire width thereof. In the illustrated embodiment, elastic means 46 are secured to the backing sheet 42 in spaced, parallel relationship to one another. Preferably, the elastic means 46 comprise a plurality of individual elastic threads secured to the backing sheet 42 by an adhesive which is applied thereto and to the backing sheet 42. Then, a center portion 48 of the elastic means 46 is stretched, and the stretched elastic means 46 are applied to the adhesive on the backing sheet 42. When the adhesive sets and the stretching is relaxed, gathers 58 (FIG. 6) are formed by the center portion 48 of the elastic means 46.

Also shown in FIG. 5 is a facing sheet 50 which has the same length and width as the backing sheet. The facing sheet 50 is composed of a non-woven material through which liquid will readily pass for absorption in the absorbent insert 38. Several sprays 52 of hot melt adhesive are applied longitudinally to the facing sheet 50, over a central portion having a width corresponding generally with the width of the absorbent insert 38. With the lines 44 and sprays 52 of hot melt in place, the components shown in FIG. 5 are assembled by positioning the absorbent insert 38 centrally on the backing sheet 42 and positioning the facing sheet 50 thereon. After assembly, these components are passed between compression rollers (not shown) to promote good bonding therebetween.

Figure 6:
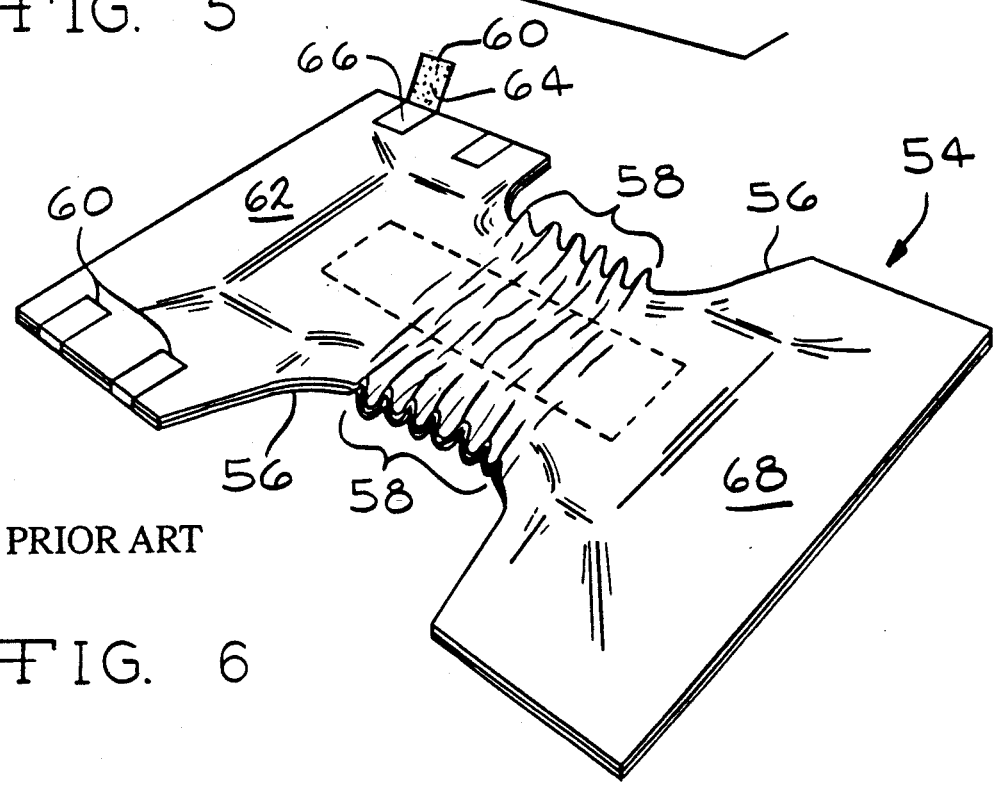
FIG. 6 is a perspective view of a completed absorbent product according to one embodiment of the present invention.

With reference to FIG. 6, an absorbent product 54 is illustrated after leg cut outs 56 have been trimmed therefrom. Gathers 58 are formed, adjacent to a central portion of the leg cut outs 56, by the central portion 48 (FIG. 5) of the elastic means 46. The gathers 58 serve to prevent leakage by promoting a snug fit of the absorbent product 54 around the legs of a wearer. Adhesive tab fasteners 60 are secured to a rear panel 62 of the absorbent product 54 in a known fashion. The tab fasteners 60 include an adhesive side 64 which remains secured to a release paper 66, until the absorbent product 54 is to be worn. With the absorbent product 54 positioned on a wearer, the tab fasteners 60 are lifted from the release paper 66 and the adhesive side 64 is applied to the outside of the backing sheet 42 on a front panel 68 of the absorbent product 54, thereby securing the absorbent product 54 to the wearer. Preferably, the adhesive on the side 64 of the tab fasteners is one which can be released from and refastened to the backing sheet 42, so that the tab fasteners 60 are refastenable.

EXAMPLE 1

An absorbent core corresponding with the core 32 was produced from cellulose fluff and Gelok 6000 double ply/double ply (1080) laminate. The super absorbent polymer in the laminate was a polyacrylate product which is distributed by Chemdal under the trade name ARIDALL 1080. The core was embossed with a 1 inch by 1 inch diamond pattern on an upper surface thereof. The channels had a width of approximately ¼ inch. Approximately 45% of the surface area of the core was constituted by channels and the remaining 55% of the surface area of the core was not channelled.

CONTROLS A, B, C, D, E, F AND G

For purposes of comparison, but not in accordance with the instant invention, several absorbent cores were produced, as described below.

Absorbent core A consisted of embossed cellulose fluff having the same base weight as the cellulose fluff used in Example 1. Core A was embossed with the same diamond pattern as the core of Example 1.

Absorbent core B comprised unembossed cellulose fluff having the same base weight as the fluff used in producing Example 1.

Absorbent core C comprised a layer of the Gelok 6000 double ply/double ply (1080) laminate on top of a cellulose fluff layer. This core differed from Example 1 only in that it was not embossed. This core corresponds with the core of a product that is distributed under the trademark Slimline.

Absorbent core D comprised a layer of embossed cellulose fluff on top of which Aridall 1080 polyacrylate super absorbent polymer had been sprinkled. The amount of super absorbent polymer was controlled to provide the same weight thereof, per square inch of the cellulose fluff, as the weight of super absorbent polymer in the Gelok 6000 double ply/double ply (1080) laminate, per square inch thereof.

Absorbent core E comprised a layer of unembossed cellulose fluff on top of which Aridall 1080 polyacrylate super absorbent polymer had been sprinkled. The amount of super absorbent polymer was controlled to provide the same weight thereof, per square inch of the cellulose fluff, as the weight of super absorbent polymer in the Gelok 6000 double ply/double ply (1080) laminate, per square inch thereof.

Absorbent core F corresponds with Example 1 except for the embossing pattern. Rather than the diamond shaped embossing pattern, absorbent core F was embossed between smooth upper and lower embossing rollers.

Absorbent core G comprises cellulose fluff which has been split into two layers, between which Aridall 1080 polyacrylate super absorbent polymer had been sprinkled. The amount of super absorbent polymer was controlled to provide the same weight thereof, per square inch of the cellulose fluff, as the weight of super absorbent polymer in the Gelok 6000 double ply/double ply (1080) laminate, per square inch thereof.

The absorbent insert of Example 1 and the absorbent cores A-G were tested for absorbency (rate), wicking and skin wetness. The procedure for each test is described below. The results of each test are set forth in Table I.

ABSORBENCY

In this test, a four inch by four inch square sample of absorbent core material, with a water impervious backing, is placed on a level surface. A test plate with a plurality of evenly spaced apertures is placed on the sample. The test plate has sides to retain a test liquid until it passes through the apertures to the absorbent core. The test liquid is a 1.0% NaCl solution. A timer is started after 10.0 milliliters of the test liquid has been introduced into the test plate. The timer is stopped when the test liquid has emptied from the test plate, through the apertures and into the absorbent core. The results of this kind of test are indicative of the rate at which an absorbent product will absorb urine. For example, an absorbent core with a 2 second time in this absorbency test will absorb urine at a faster rate than an absorbent core with a 5 second time in this absorbency test.

SKIN WETNESS

In this test, a three inch by five inch rectangular sample of absorbent core, with a water impervious backing, is placed on a level surface. In the center of the sample, a 50 milliliter sample of a 1.0% NaCl solution is deposited at the rate of 7.0 milliliters per second. Absorbent paper toweling is cut into three inch by five inch rectangles and a stack of the paper toweling weighing approximately eighteen grams is weighed and its dry weight is recorded. Sixty seconds after the 1.0% NaCl solution has been deposited on the absorbent core sample, a previously weighed stack of paper toweling is placed on top of the absorbent core sample and a three inch by five inch rectangular five pound weight is placed on top of the paper toweling. After fifteen seconds, the weight is removed from the then wet paper toweling which is reweighed. The weight of the dry toweling is subtracted from the weight of the wet paper toweling to give a skin wetness number corresponding with the weight of 1.0% NaCl solution which was released by the absorbent core into the paper toweling. A low number indicates that an absorbent core has good retention of liquid so that adjacent skin will stay relatively dry while a high number indicates that liquid is readily released from an absorbent core so that adjacent skin will become relatively wet.

WICKING

In this test, a seven inch by seven inch square sample of absorbent core, with a water impervious backing, is placed on a level surface. A 25.0 milliliter sample of 1.0% NaCl solution including a blue dye is dispensed from a burette into the center of the sample at the rate of 10.0 milliliters per second. The tip of the burette is ¼ inch from the surface of the absorbent core sample, to prevent spattering of the test liquid. One minute after the test liquid has been dispensed, the perimeter of the wet spot is marked and measurements are taken along a first axis and a second axis which is angularly displaced ninety degrees from the first axis. Thus, the results of this test are expressed in terms of two measurements. A pair of small measurements for an absorbent core indicates that the core does a relatively poor job of distributing or wicking fluid so that fluid may puddle in one area of the absorbent core while the absorptive capacity of remote, dry areas of the absorbent core is wasted. Conversely, a pair of large measurements for an absorbent core indicates that the core does a relatively good job of wicking fluid so that liquid will be well distributed throughout the absorbent core.

|  | ABSORBENCY (time in seconds until fully absorbed) | SKIN WETNESS (grams of liquid absorbed by toweling) | WICKING | |
|---|---|---|---|---|
|  |  |  | (side-to side diameter of liquid) | (top to bottom diameter of liq.) |
| EXAMPLE 1 | 2.3 | 12.4 | 5¾" | 6" |
| CORE A | 1.5 | 19.0 | 4" | 4" |
| CORE B | 1.7 | 19.3 | 3½" | 3½" |
| CORE C | 5.5 | 9.0 | 4¼" | 4¼" |
| CORE C | 5.0 | — | — | — |
| CORE C* | — | 2.2 | 3¼" | 4¼" |
| CORE D | 1.8 | 12.1 | 3½" | 3½" |
| CORE E | 1.4 | 11.3 | 3" | 3¼" |
| CORE F | 1.3 | — | — | — |
| CORE F* | — | 8.4 | 5¾" | 4" |
| CORE G | 2.0 | 14.2 | 3¼" | 2¾" |

(Note: the core identifications which are followed by an asterisk represent absorbent cores which were produced from laminate from a different batch than the laminate which was incorporated in the other absorbent cores for which test results are reported in Table 1. As a comparison of the skin wetness numbers for the first and third "Core C" structures suggests, the laminate which was incorporated in the cores marked by an asterisk had a higher concentration of super absorbent polymer than the laminate which was incorporated in the other cores. Accordingly, comparisons between results for cores marked by an asterisk and cores which are not so marked, should take this into account.)

The results set forth in Table I for absorbency demonstrate that unembossed Core C has relatively poor absorbency, while the core of Example 1 has relatively good absorbency. Of the cores that included a layer of laminate, only Core F had a better absorbency number than the example 1 core. It is theorized that the channel areas in Example 1 promote a rapid absorption of liquid through the laminate layer into the fluff layer. Core F, embossed with flat rollers, simulates the channels in Example 1 and the rapid absorption of liquid into Core F supports the theory that there is very fast absorption through the channels.

There is a drawback to the structure of Core F, however, and this is demonstrated by a comparison of Skin Wetness numbers for Core C* and Core F*. Core C* only gave up 2.2 grams of liquid, while Core F* gave up 8.4 grams. This indicates that Core C* with no channels retains liquid much better than Core F* which corresponds with 100% channels. Thus, after 1 minute, liquid can flow back through the laminate, out of Core F*, whereas Core C* with no channels gave up very little liquid in the Skin Wetness test.

The embossing pattern of the Example I core includes a continuous network of channels which exhibits a demonstrated ability to promote good wicking. In fact, Example 1 core had the best wicking numbers although, as indicated in Table I, a direct comparison between Cores C* and F* and the other cores is unwarranted.

Additional samples of cores were separately produced and tested. The additional cores corresponded with the Example I core, Core B and Core C. Some of the cores corresponding with Core C and the Example I core were subjected to the Skin Wetness test described above while others of those cores were subjected to a modified Skin Wetness test in which the toweling and the five pound weight were placed on the specimens ten minutes after wetting, instead of one minute after wetting. The results are set forth below in Table II.

TABLE II

|  | 1 MINUTE SKIN WETNESS (grams) | 10 MINUTE SKIN WETNESS (grams) |
|---|---|---|
| Example I | 6.7 | 3.0 |
| Core C | 3.5 | 1.6 |

The results set forth in Table II demonstrate that the super absorbent polymer continues to absorb liquid after one minute after a wetting. Accordingly, over time, the Skin Wetness performance of the Example I core approaches that of Core C. One minute after wetting, the Example I core gave up 3.2 grams more of liquid than Core C while, ten minutes after wetting, the Example I core gave up only 1.4 grams more of liquid than Core C. These results demonstrate that the Example I core, in addition to exhibiting much better Absorbency than Core C, exhibits Skin Wetness performance which is comparable to Core C, ten minutes after wetting.

An additional set of core samples were separately produced and tested for their ability to absorb multiple wettings. The test procedure corresponded with the Absorbency test procedure outlined above, except that, before the timer is started and ten minutes after the initial wetting, an additional 10 milliliters of liquid was deposited on the core. Then, the timer was started and the time required for the second ten milliliter wetting to be absorbed was recorded. The results of this test, for cores corresponding with Example I, Core B and Core C, are set forth in Table III.

TABLE III

|  | ABSORBENCY (for a second 10 ml wetting) (seconds) |
|---|---|
| Example I | 19.6 |
| Core B | 6.0 |
| Core C | >120.0 (not all liquid was absorbed after 2 minutes) |

The results set forth in Table III suggest that the channels in the Example I core continue to serve as transfer sites through which liquid can be absorbed, even after an initial wetting. Core C, on the other hand, exhibits an inability to absorb a second wetting. This is believed to be due to "gel-blocking" where swollen, gelled super absorbent polymer particles coalesce to form a layer which blocks additional liquid from being absorbed by the core. Although Core B has excellent Absorbency for a second wetting, Core B cannot hold liquid under pressure, as shown by the data in Table I.

Figure 7:
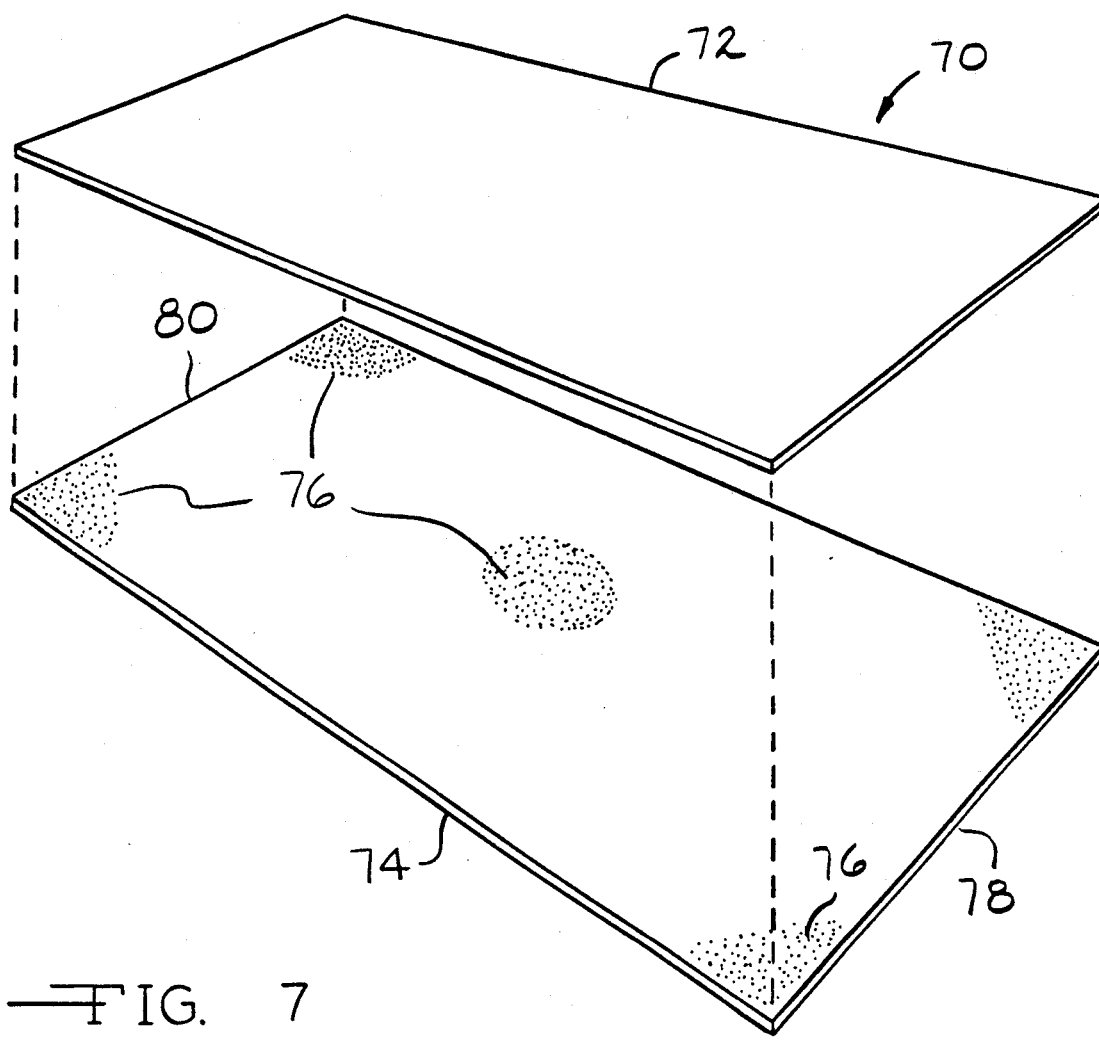
FIG. 7 is an exploded perspective view of the absorptive components of a second embodiment of an absorbent product according to the present invention.
Figure 8:
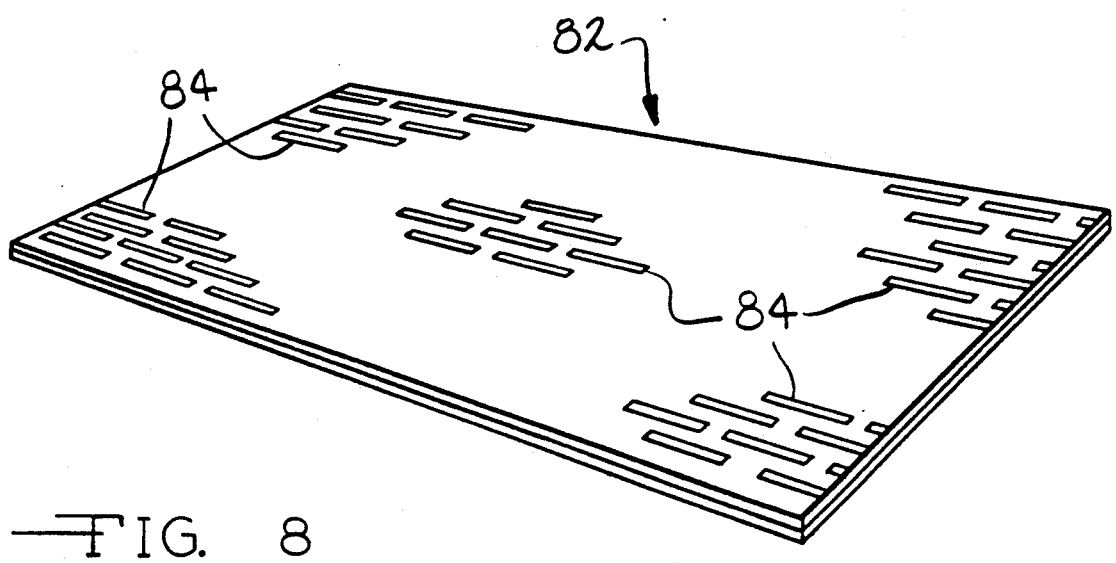
FIG. 8 is a perspective view of the absorptive components illustrated in FIG. 7 after they have been joined together by an embossing operation.

With reference to FIG. 7, the absorptive components of an absorbent product according to a second embodiment of the invention are indicated generally at 70. In this embodiment, the absorptive components 70 comprise an upper layer 72 and a lower layer 74 of thick, air-laid tissue and, on top of the layer 74, a layer of super absorbent polymer particles, represented by dots 76 in the middle and the four corners of the layer 74. The polymer particles can be relatively evenly distributed over the entire layer 74 although the polymer layer need not extend to the reaches of the two ends, 78 and 80 of the layer 74. With the polymer powder in place on the layer 74, the layer 72 is united with the layer 74 and embossed to produce an absorbent core 82, shown in FIG. 8.

A preferred embossing pattern is represented by bars 84 in the middle and the four corners of the core 82. The bars 84 correspond with areas of compression created during the embossing step. Surrounding the bars 84 are uncompressed, tufted areas. The side of the core 82 not illustrated in FIG. 8 has a smooth surface.

Figure 9:
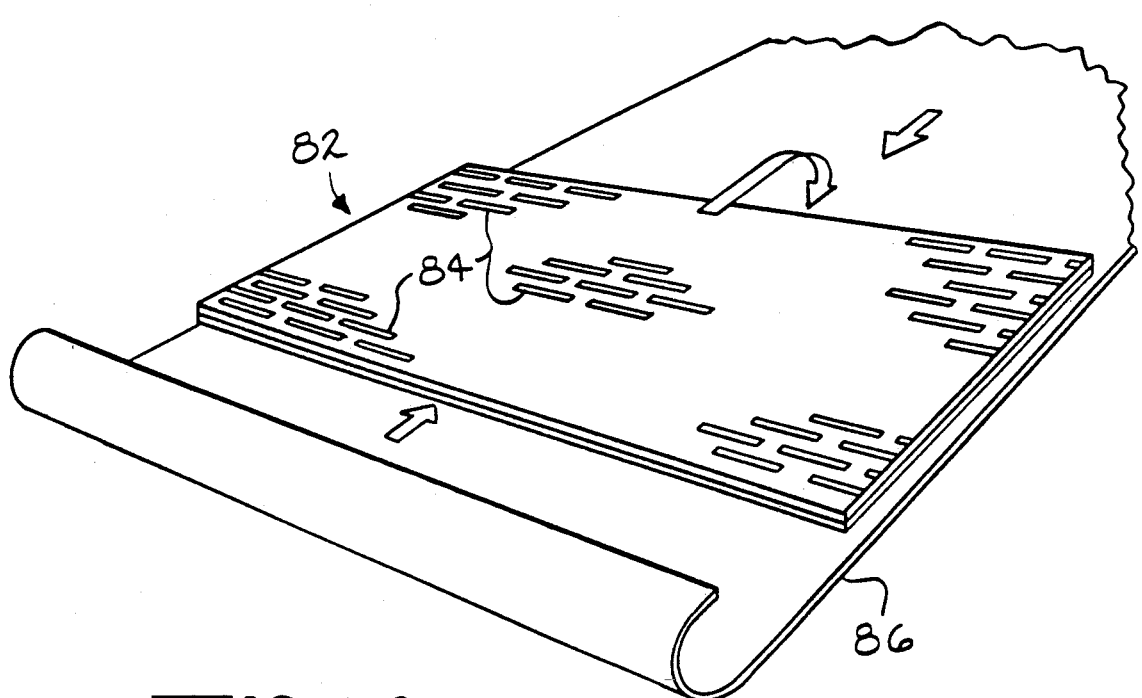
FIG. 9 is a perspective view of a tissue wrapping operation applied to the embossed components illustrated in FIG. 8.
Figure 10:
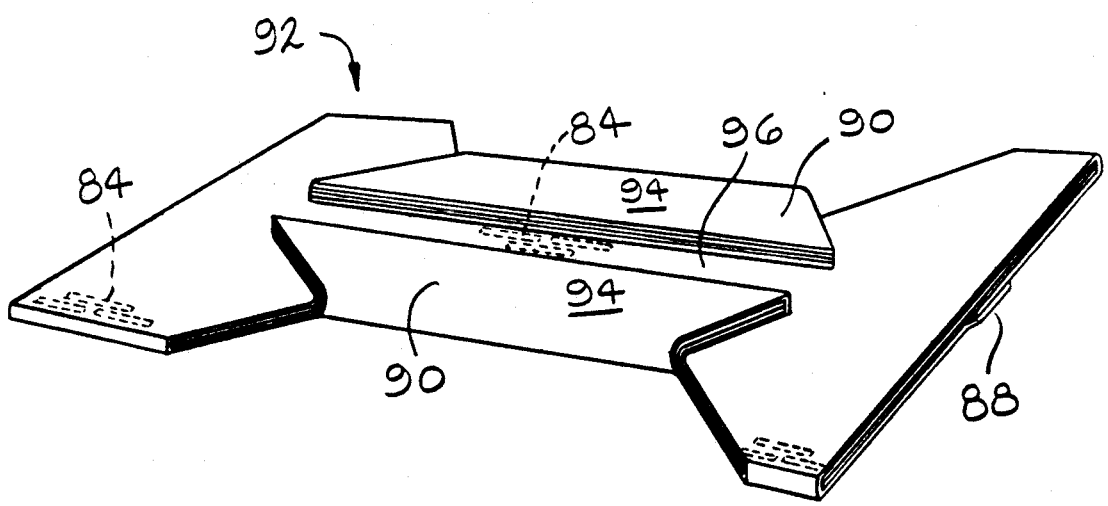
FIG. 10 is a perspective view of the embossed components after a cutting and folding operation.

With reference to FIG. 9, a tissue wrapping operation is illustrated in which tissue paper 86 is wrapped around the absorbent core 82. When the core 82 is completely wrapped, excess tissue 86 is trimmed and the ends of the wrapped tissue 86 are glued or otherwise secured to produce a seam 88, shown in FIG. 10. The wrapped core 82 is slit to define lateral regions 90 which are folded inwardly, opposite the seam 88, to produce an absorbent insert 92. When the lateral regions are folded inwardly, a smooth surface 92 is exposed. The slitting and folding steps are controlled so that a substantial gap remains between the edges of the lateral regions 90 to define a central region 94. The exposed surface in the central region 94 includes compressed areas represented by the bars 84.

Figure 11:
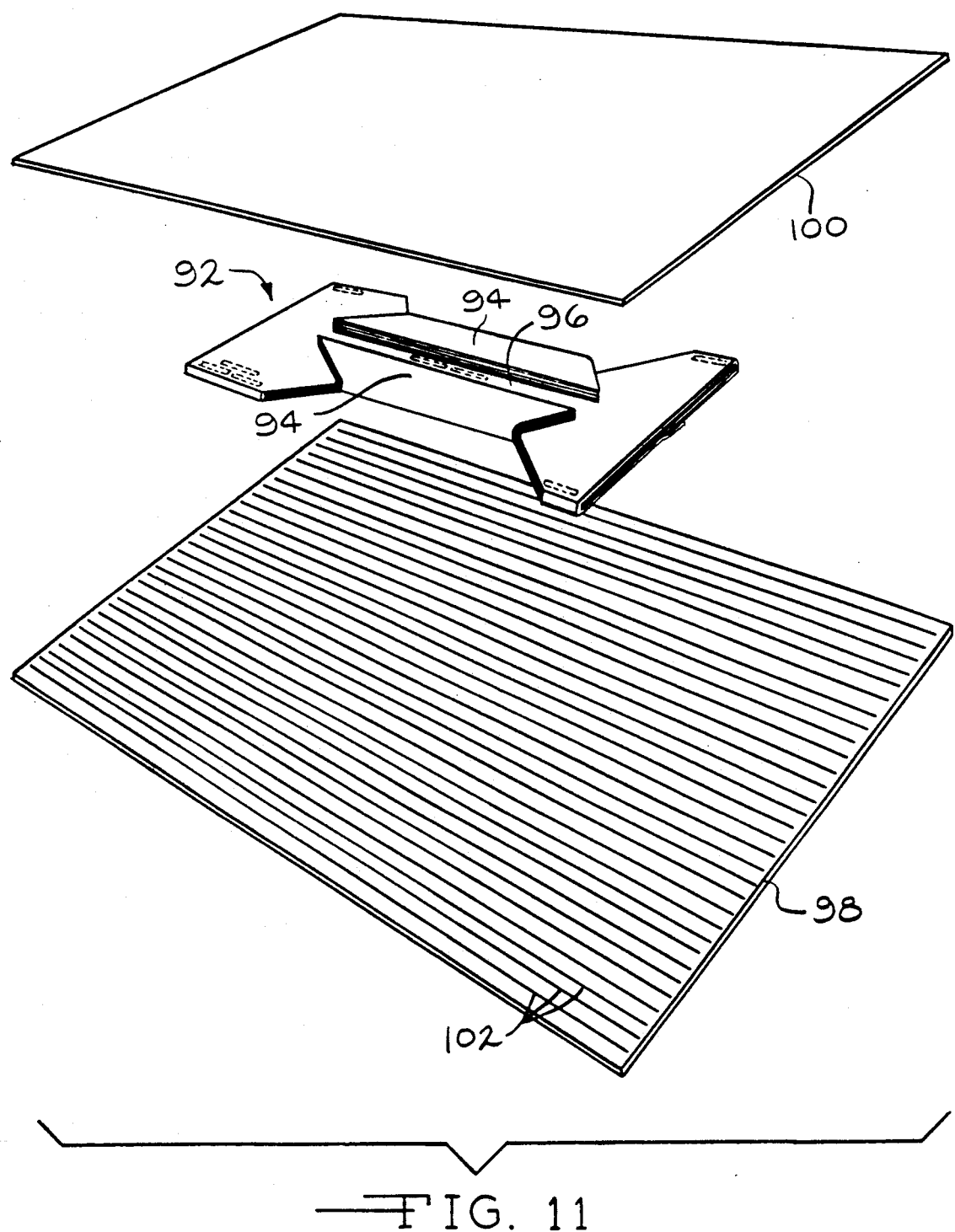
FIG. 11 is an exploded, perspective view of a second embodiment of an absorptive product incorporating the tissue wrapped, embossed absorptive components illustrated in FIG. 10.

An absorbent article can be produced from the absorbent insert 92, by sandwiching it between a water impervious backing sheet 98 and a non-woven facing sheet 100. Lines 102 of hot melt adhesive are applied to the backing sheet 98 to adhesively secure it to the absorbent insert 92 and the facing sheet 100. If desired, elastic means (not shown) corresponding with the means 46 (FIG. 5) can be applied to the backing sheet 98 (FIG. 11) to produce gathers in a finished absorbent product.

After the insert 92 has been assembled between the backing sheet 98 and the facing sheet 100, leg cut outs would be trimmed from the assembly, as discussed above with reference to FIG. 6.

Figure 12:
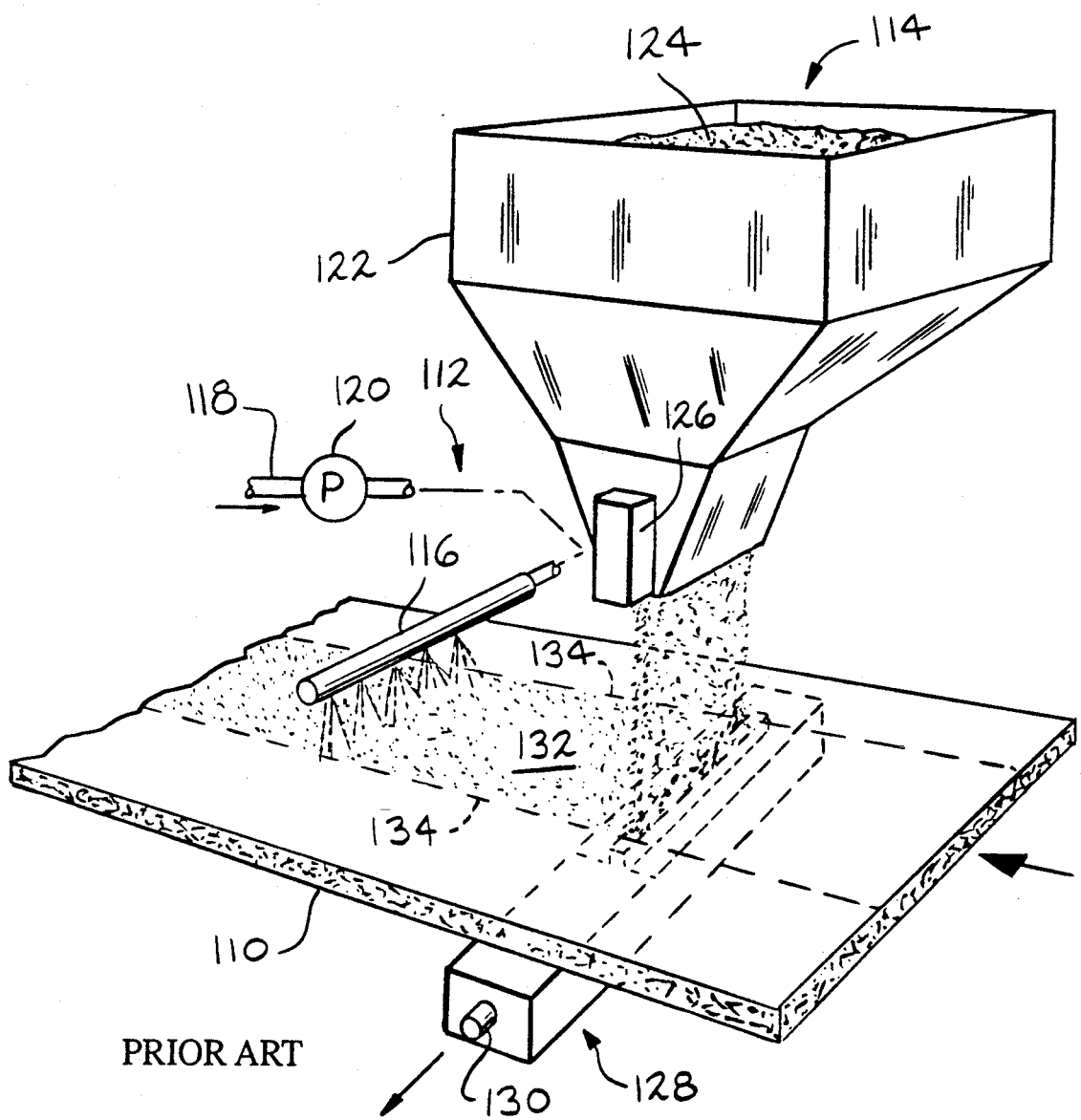
FIG. 12 is a perspective view of apparatus for depositing polymer to produce one of the absorptive components of third and fourth embodiments of an absorbent product according to the present invention.

Referring now to FIG. 12, the direct deposition of a super absorbent polymer onto a fluff layer 110 will now be described. Layer 110 is a relatively thick layer of moisture absorbing material, such as cellulose fluff, fluffed wood pulp, batting or the like.

Apparatus for use in depositing polymer powder on the fluff layer 110 comprises water spray means indicated generally at 112 and polymer deposition means indicated generally at 114. The water spray means comprises a spray head 116 to which water is supplied through conduit 118 at a constant pressure which may be monitored or controlled by a pressure controller 120. The polymer deposition means 114 comprises a trough 122 for holding polymer powder, indicated at 124, and deposition rate control means 126 for adjusting the rate at which polymer powder 124 is released from the trough 122. Beneath the polymer deposition means 114, specifically, the trough 122, there is provided a vacuum integration means 128 for drawing a vacuum below the fluff layer to draw polymer powder 124 into the fluff layer where the fluff fibers will engage and retain it. A central conduit 130 in the vacuum integration means 128 can be connected to a suitable vacuum source (not shown).

Figure 13:
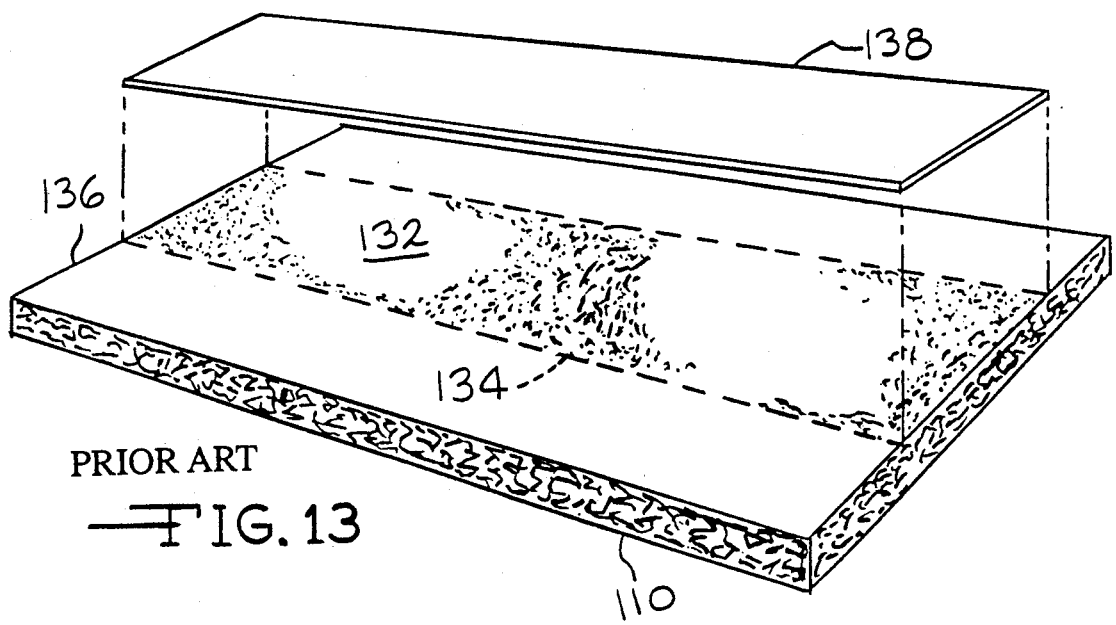
FIG. 13 is a perspective view of absorbent components of a third embodiment of the invention, including a component produced on the apparatus illustrated in FIG. 12.

The water spray means 112 and the polymer deposition means 114 are positioned and sized to spray water and deposit polymer powder on the fluff layer 110 in a central region 132 defined between dotted lines 134. The polymer deposition means 114 may be operated continuously, or intermittently so that discreet absorbent portions of the central region 132 having polymer powder 124 deposited thereon are separated by discreet portions of the central region 132 which do not have polymer powder 114 deposited thereon. Continuous operation of the polymer deposition means 114 will produce a continuous layer of polymer powder 124 in the central region 132 of a piece 136 which has been cut from the fluff layer 110, as shown in FIG. 13. Intermittent deposition of polymer powder 124 could be used to produce a piece, like the piece 136, except that the polymer powder 124 would not extend all of the way to the edges; it would be recessed from all four sides of the piece.

During operation of the FIG. 12 apparatus, fluff material constituting the layer 110 is advanced from right to left, passing first under the polymer deposition means 114 and then under the water spray means 112. By controlling the rate of deposition of polymer powder 124, relative to the rate at which the fluff layer is advanced, one can achieve a desired concentration of polymer powder in the fluff material 110. In the central region, a concentration of approximately 130 grams of polymer (Aridall 1080 polyacrylate super absorbent polymer) per square meter is a good concentration. More or less polymer may be used, depending on a number of factors including the identity and capacity of the super absorbent polymer and the intended use.

After the polymer powder 124 is deposited in the central region 132 of the layer 110, water or an aqueous solution of a water soluble adhesive is sprayed on the central region. The water or the like promotes bonding between the fibers constituting the layer 110 and the polymer powder. Additionally the water or the like plays an important role during an embossing operation which is described below.

Figure 14:
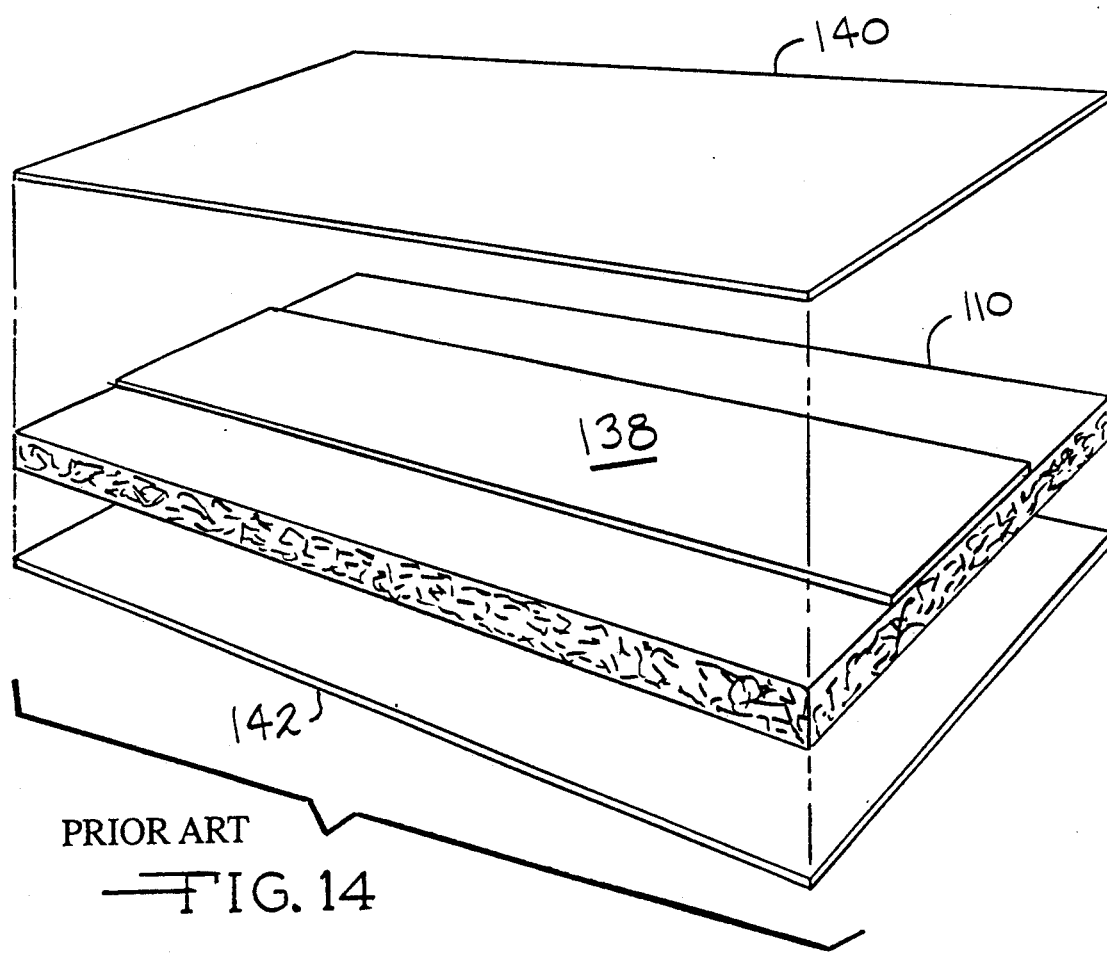
FIG. 14 is an exploded, perspective view of the absorptive components illustrated in FIG. 13, and upper and lower tissue layers.

With further reference to FIG. 13, there is illustrated a layer 138 of heavy tissue, corresponding in size with the central region 132. As illustrated in FIG. 14, the tissue layer 138 is positioned on the piece 136 so that it covers the central region 132 and the polymer powder 124 deposited thereon. The layer 138 is positioned on the same side of the fluff layer 110 as that on which the polymer powder 124 was deposited. The layer 138, as well as the layer 24 (FIG. 1) can be single ply or double ply. If single ply, the tissue should have a basis weight of between 14 pounds and 18 pounds. If double ply, the tissue should have a basis weight of between 14 pounds and 22 pounds. A single ply tissue with a basis weight of 14.5 pounds produces very good results. The tissue layers 138 and 24 (FIG. 1) should consist of a tissue with good stretchability; 18% to 33% machine direction stretch is preferred.

In FIG. 14, upper and lower tissue layers 140 and 142 are positioned to be brought into contact with the upper and lower surfaces of the piece 136. The tissue layers 140 and 142 are light by comparison with the tissue layer 138. A 12 pound basis weight wet strength tissue is preferred for the layers 140 and 142 as well as for the layers 28 and 30 (FIG. 2) and the tissue wrap 86 (FIG. 9).

After the tissue layers 140 and 142 are brought into contact with the piece 136, the components are subjected to an embossing step. A smooth roller (not shown) is applied to the lower tissue layer 142 and a patterned roller (not shown) is applied to the opposed, upper tissue layer 140 to produce an embossed absorbent core 144. A suitable diamond embossing pattern is shown in FIG. 15, reflected in the pattern shown on the surface of the tissue layer 140. The embossing pattern on the embossing die (not shown) applied to the upper tissue layer 140 produces a pattern of channels 146 in the tissue layer 140, the tissue layer 138, and the fluff layer 110. As is explained above, these channels 146 constitute transfer sites through which liquid is absorbed quickly from above the upper tissue layer 140, through the tissue layer 138, to the fluff layer 110 where it will be absorbed, eventually by the polymer powder 124 dispersed therein. The channels 146 are interconnected in a continuous network which promotes excellent wicking characteristics.

In the channels 146, there is a high density interface between the tissue layers 138 and 140 and the fluff layer 110. In this interface, there is a physical bond between the layers 138, 140 and 110 which gives the absorbent core 144 physical integrity. In the areas between the channels 146, the layers 138, 140 and 110 have a lower density than these layers have in the channels 146. The polymer powder 124 is, in effect, laminated between the tissue layer 138 and the fluff layer 110. This core construction is advantageous because migration of the powder 124 is resisted while swelling of the powder 124 is relatively unrestricted. The channels 146 promote fast absorption. This core construction also provides very high capacity with an ability to absorb multiple wettings. These characteristics are believed to be due, in part, to what amounts to a three dimensional distribution of polymer powder in the core 144, as opposed to a two dimensional distribution of polymer powder in absorbent products which include a super absorbent polymer laminated between two tissue layers. In the former, there is a degree of freedom for the polymer to expand into the fluff layer whereas, in the latter, the polymer is stuck between two tissue layers in a substantially two-dimensional plane. For example, Core C is an absorbent core which included a super absorbent laminate with super absorbent polymer sandwiched between tissue layers. As the results set forth in TABLE III indicate, core C could not absorb a second wetting, even after two minutes. It appeared that the super absorbent polymer in the laminate layer in Core C had expanded and coalesced to form a two-dimensional barrier layer through which liquid could not pass. In contrast, the super absorbent polymer in the core 144 is not confined in a two-dimensional plane. Consequently, the core 144 can absorb multiple wettings.

The core 144 has good skin wetness performance, i.e., it retains fluid well, even under pressure. It is believed that the three-dimensional distribution of super absorbent polymer in this core construction allows the polymer to have greater capacity because there is more room for the polymer to expand. Once liquid is taken up by the super absorbent polymer, the liquid is not released, even under pressure. Liquid that is not picked up by the polymer will be held in the fluff layer. Although liquid can be squeezed out of fluff, this core construction resists the squeeze out of liquid, back through the upper tissue layer 140. The polymer powder in the core 144 is concentrated on and near the upper surface of the fluff layer 110. When the absorbent core is not under pressure, the polymer is distributed in three-dimensions, as discussed above. However, when the core is compressed after a wetting, the gelled, swollen polymer particles will be brought into close contact forming a barrier layer to prevent the squeeze out of liquid through the upper tissue layer 140.

The embossing step can be carried out advantageously with approximately 50 to 175 lbs of pressure per lineal inch of the embossing rollers. A variety of patterns would be suitable for the patterned embossing roller, beside the one reflected in the upper tissue layer 140 shown in FIG. 15.

It will be appreciated that the manufacturing steps described above with reference to FIGS. 12–15 can be applied to bulk materials supplied, for example, from rolls. Specifically, the fluff layer 110, the tissue layers 138, 140 and 142 can be manufactured into an embossed, absorbent core 144 of infinite length which can later be cut to appropriate length and incorporated into an absorbent product according to the instant invention. After the absorbent core 144 has been embossed, it is preferably subjected to a de-bulking operation in which it is passed between two compression rollers (not shown). This step adds further integrity to the embossed absorbent core 144 and promotes more economical packaging by producing thinner absorbent products.

Referring now to FIG. 16, the embossed absorbent core 144 is illustrated after ears 148 have been trimmed therefrom to produce an absorbent insert 150, with leg cut outs 152, for incorporation in an absorbent product. The cut outs 152 extend inwardly toward, but terminate just short of, the central region 132 defined between the dotted lines 134. The ears 148 can be recycled, if desired, to yield material suitable for producing additional fluff layers 110. The trimming can be carried out with a die-cutter which may include a cutter for cutting the embossed absorbent core 144 to produce an absorbent insert 150 of a given length. Alternatively, a separate cutter may be used to cut absorbent core material to an appropriate length.

As used hereinabove, the term fluff refers to a web made up of loose fibers. It is also intended to encompass composite webs made up of such fibers and including other materials such as synthetic fibers. For example, Hercules distributes, under the name Pulpex, a polyethylene/polypropylene blend of fibers which can be advantageously incorporated into a fluff layer. Pulpex, in amounts of five percent can be incorporated into fluff and heated to improve the integrity of the fluff layer.

Figure 17:
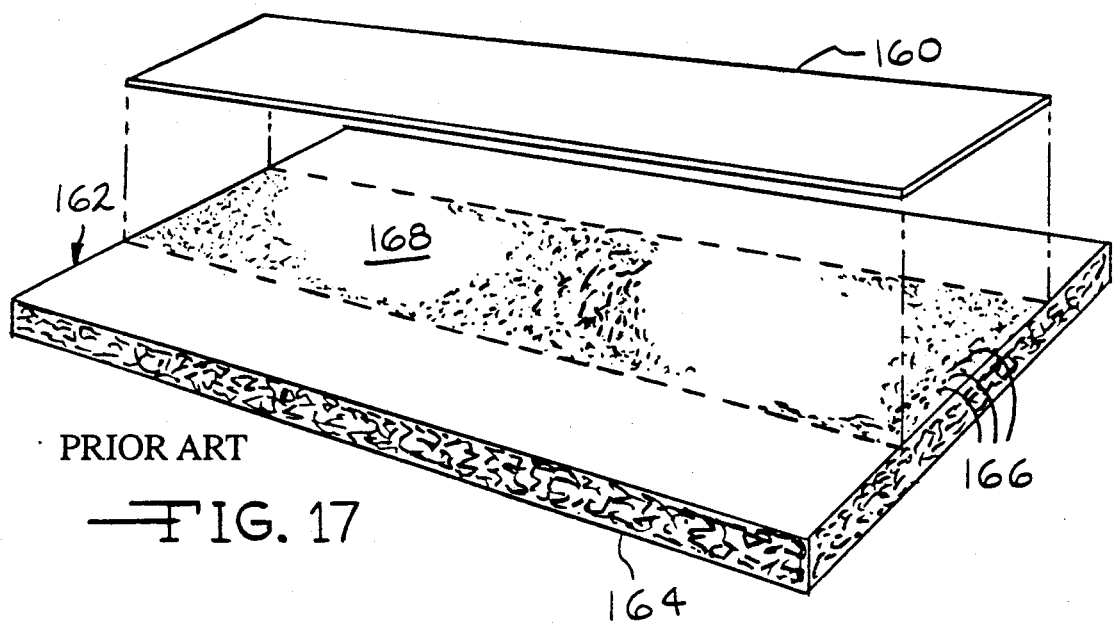
FIG. 17 is a perspective view of absorbent components of a fourth embodiment of the invention, including a component produced on the apparatus illustrated in FIG. 12.

With reference to FIG. 17, another embodiment of an absorbent core comprises a layer 160 of laminate and piece 162 consisting of a fluff layer 164 and super absorbent polymer powder 166 deposited in a central region 168 of the fluff layer 164. The piece 162 can be readily produced on apparatus of the type described above with reference to FIG. 12. It will be appreciated that the apparatus of FIG. 12 can be operated so that it intermittently deposits polymer powder 166 on the central region 168 of the layer of fluff 164. In that case, the layer of polymer powder 166 would terminate short of the ends of the piece 162, as well as terminating short of the sides of the piece 162, as shown in FIG. 17.

Figure 18:
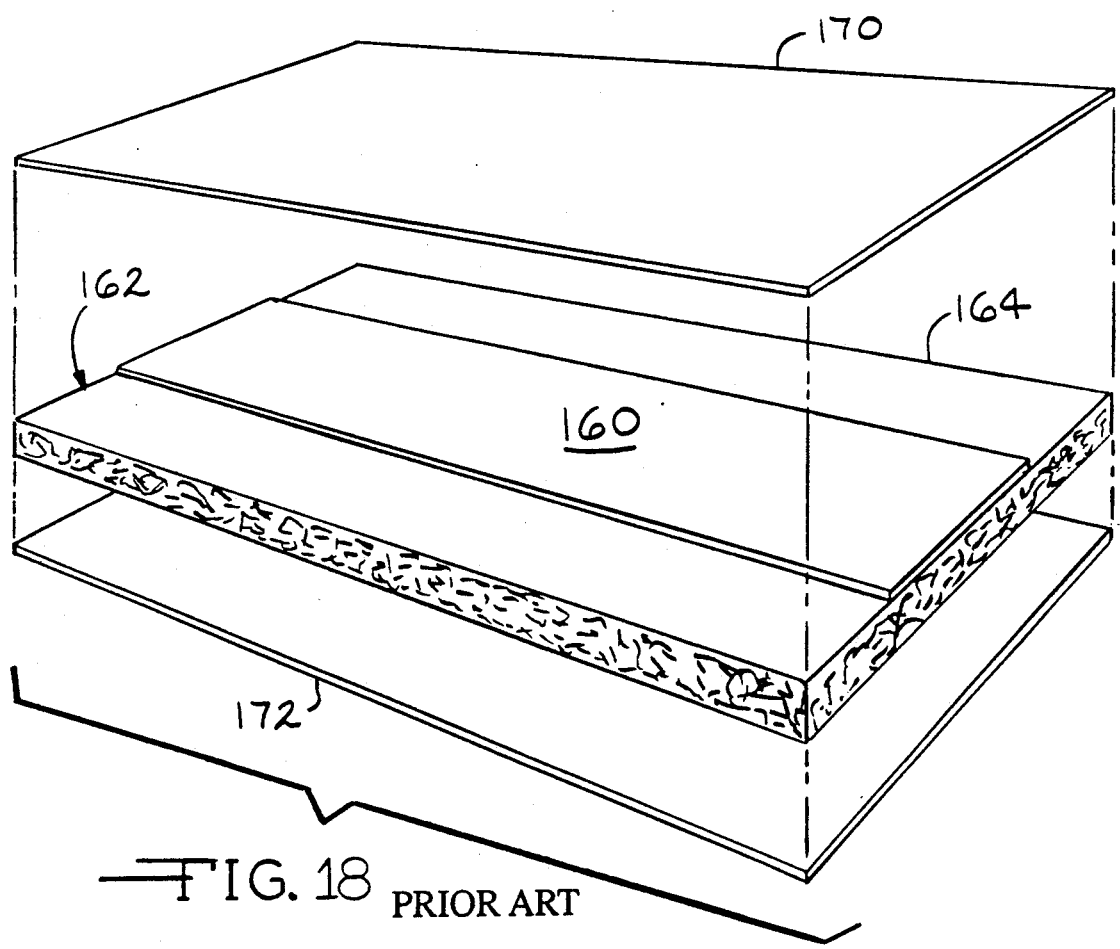
FIG. 18 is an exploded, perspective view of the absorptive components illustrated in FIG. 17, and upper and lower tissue layers.

The laminate layer 160 comprises super absorbent polymer powder dispersed in and supported on a heavy tissue. Preferable, the layer 160 of laminate is Gelok 6000 single ply/double ply, a laminate consisting of 1080 polyacrylate super absorbent polymer sandwiched between a single ply of 14 pound basis weight tissue and two sheets of 10.5 pound basis weight tissue. The laminate layer corresponds in size with the central region 168 where the polymer powder 166 is deposited. As illustrated in FIG. 18, the laminate layer 160 is positioned on the piece 162 so that it covers the central region 168 and the polymer powder 166 deposited thereon. The laminate layer 160 is positioned on the same side of the fluff layer 164 as that on which the polymer powder 166 was deposited. The laminate layer can be single ply or double ply. If single ply, the tissue should have a basis weight of between 14 pounds and 18 pounds. If double ply, the tissue should have a basis weight of between 14 pounds and 22 pounds. A single ply tissue with a basis weight of 14.5 pounds produces very good results. The laminate layer 160 should consist of a tissue with good stretchability; 18% to 33% machine direction stretch is preferred.

In FIG. 18, upper and lower tissue layers 170 and 172 are positioned to be brought into contact with the upper and lower surfaces of the piece 162. Optionally, a single ply of heavy tissue (not shown) can be positioned between the piece 162 and the tissue layer 170. The tissue layers 170 and 172 are light by comparison with the tissue incorporated into the laminate layer 160. A 12 pound basis weight wet strength tissue is preferred for the layers 170 and 172.

After the tissue layers 170 and 172 are brought into contact with the piece 162, the components are subjected to an embossing step. A smooth roller (not shown) is applied to the lower tissue layer 172 and a patterned roller (not shown) is applied to the opposed, upper tissue layer 170 to produce an embossed absorbent core 174 shown in FIG. 19. A suitable diamond embossing pattern is shown in FIG. 19, reflected in the pattern shown on the surface of the tissue layer 170. The embossing pattern on the embossing die (not shown) applied to the upper tissue layer 170 produces a pattern of channels 176 in the tissue layer 170, the laminate layer 160, and the fluff layer 164. These channels 176 constitute transfer sites through which liquid is absorbed quickly from above the upper tissue layer 170, through the laminate layer 160, to the fluff layer 164 where it will be absorbed, eventually by the polymer powder 166 dispersed therein. The channels 176 are interconnected in a continuous network which promotes excellent wicking of deposited fluid, through the channels, to portions of the embossed absorbent core 174 remote from the deposit site. The polymer powder which is deposited in the fluff layer locks in liquid which is absorbed throughout the channels 176 to yield excellent skin dryness characteristics for the absorbent core 174, while the channels 176 provide excellent absorbency characteristics. Moreover, as demonstrated in Table III, an absorbent core (Example I) which has been embossed to provide channels, can absorb multiple wettings.

In the channels 176, there is a high density interface between the laminate layer 160, the tissue layer 170 and the fluff layer 164. In this interface, there is a physical bond between the layers 160, 170 and 164 which gives the absorbent core 174 physical integrity. In the areas between the channels 176, the layers 160, 170 and 164 have a lower density than these layers have in the channels 176. The polymer powder 166 that has been deposited on the fluff layer 164 is, in effect, laminated between the laminate layer 160 and the fluff layer 164. This core construction is advantageous because migration of the deposited powder 166 is resisted while swelling of the deposited powder 166 is relatively unrestricted. The channels 176 provide the absorbent insert with excellent absorbency. This core construction also provides very high capacity with an ability to absorb multiple wettings. These characteristics are believed to be due, in part, to what amounts to a three dimensional distribution of polymer powder in the core 144, as opposed to a two dimensional distribution of polymer powder in absorbent products which include a super absorbent polymer laminated between two tissue layers. Thus, the absorbent core 174 combines the high capacity afforded by super absorbent polymer dispersed in fluff with the excellent skin wetness and core integrity afforded by the embossed laminate/fluff structure.

The embossing step can be carried out advantageously with approximately 50 to 175 lbs of pressure per lineal inch of the embossing rollers. A variety of patterns would be suitable for the patterned embossing roller, beside the one reflected in the upper tissue layer 170 shown in FIG. 19.

It will be appreciated that the manufacturing steps described above with reference to FIGS. 17-19 can be applied to bulk materials supplied, for example, from rolls. Specifically, the fluff layer 164, the laminate layer 160, the tissue layers 170 and 172 can be manufactured into an embossed, absorbent core 174 of infinite length which can later be cut to appropriate length and incorporated into an absorbent product according to the instant invention. After the absorbent core 174 has been embossed, it is preferably subjected to a de-bulking operation in which it is passed between two compression rollers (not shown). This step adds further integrity to the embossed absorbent core 174 and promotes more economical packaging by producing thinner absorbent products.

Referring now to FIG. 20, the embossed absorbent core 174 is illustrated after ears 178 have been trimmed therefrom to produce an absorbent insert 180, with leg cut outs 182, for incorporation in an absorbent product. The cut outs 182 extend inwardly toward, but terminate just short of, the layer 160 of laminate. The ears 178 can be recycled, if desired, to yield material suitable for producing additional fluff layers 164. The trimming can be carried out with a die-cutter which may include a cutter for cutting the embossed absorbent core 174 to produce an absorbent insert 180 of a given length. Alternatively, a separate cutter may be used to cut absorbent core material to an appropriate length.

The absorbent inserts 150 and 180 can readily be incorporated in a diaper product such as the absorbent product 54 shown in FIG. 6. Alternatively, these inserts can be sandwiched between a layer of non-woven material and poly backing to produce pad products, such as a bed pad, without leg cut outs 56 as provided for the absorbent product 54.

Figure 21:
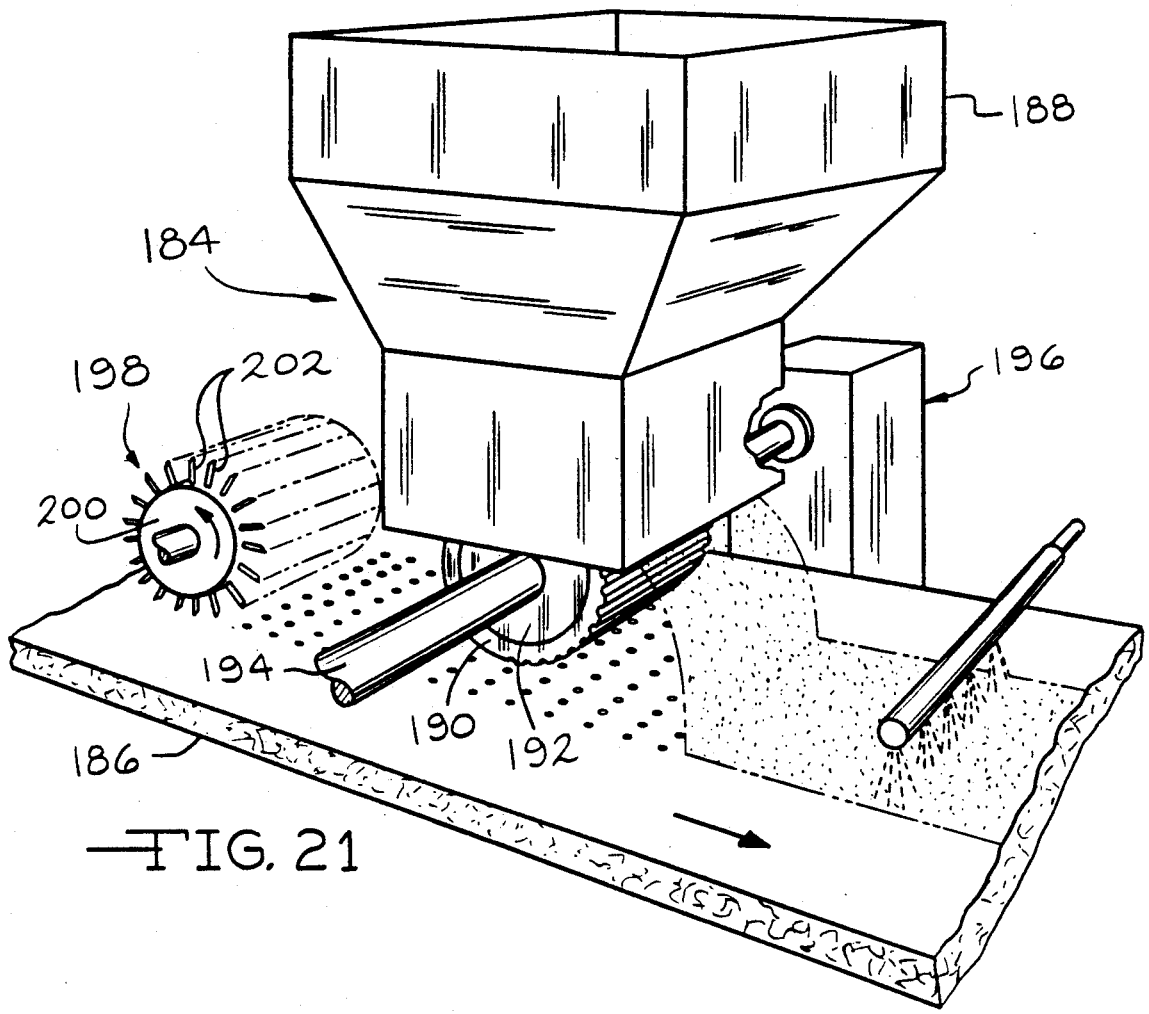
FIG. 21 is a perspective view of apparatus for depositing polymer in a given concentration in a target area and in a concentration less than the given concentration in areas adjacent to the target area, to produce an absorptive component of an absorbent product according to a preferred embodiment of the present invention.

Referring now to FIG. 21, apparatus for depositing superabsorbent polymer in pre-selected, differing concentrations is indicated generally at 184. A continuous layer of fluff 186 is supported on a conveyor (not visible) on which it is advanced at a substantially constant rate from left to right, as indicated by an arrow. A superabsorbent polymer powder hopper 188 is supported above the conveyor and the fluff layer 186. Dosing means comprising a dosing cylinder 190 and pair of end plates 192 (one is visible in FIG. 21) are positioned at the bottom of the hopper 188 and a portion of the dosing means extends upwardly into the hopper as shown more clearly in FIGS. 23 and 24. The dosing cylinder 190 and the end plates 192 are concentrically mounted about a shaft 194 which is rotated by drive means, indicated generally at 196, at a substantially constant rate of speed relative to the rate at which the fluff layer 186 is conveyed from left to right.

Figure 22:
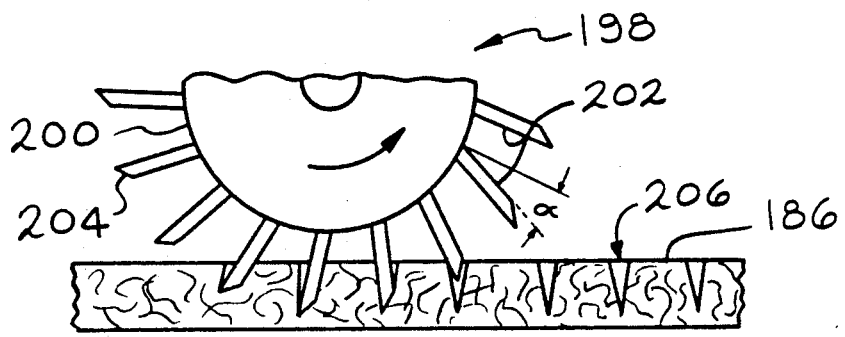
FIG. 22 is a side elevational view of a "picker wheel" which is useful for preparing a layer of fluff to have superabsorbent polymer deposited thereon and therein.

Ahead of the dosing means, a picker wheel, indicated generally at 198, is mounted above the fluff substrate, for rotation in the direction indicated by the arrow (counterclockwise as viewed in FIGS. 21 and 22). The picker wheel 198 comprises a central cylinder 200 and a plurality of picks 202 supported in the cylinder 200 and extending generally in a radial direction from the cylinder 200. Good results have been obtained with picks comprising one quarter inch diameter rods supported on the cylinder 200, spaced on 1 inch centers and extending approximately one and one half inches from the surface of the cylinder 200 in a substantially radial direction. Actually, as shown in FIG. 22, it is preferred that the picks be offset from a radial orientation so that a free end 204 having a beveled surface is offset by an angle alpha of approximately 5 to 15 degrees from a radial direction, as shown in FIG. 22. This orientation facilitates removal of the picks 202 from the fluff layer 186 as it moves from left to right in FIG. 22 and the picker wheel is rotated in a counterclockwise direction. The bevelled surface on the free end 204 also facilitates removal of picks from, as well as penetration of picks into, a fluff layer. It is preferred that the picks 202 extend wholly within planes which are normal to the fluff layer 186 and the conveyor on which it is supported.

The action of the picker wheel creates depressions indicated generally at 206 and the depressions extend a substantial distance into the fluff layer. Consequently, a small percentage of superabsorbent polymer particles deposited on the fluff layer 186 will tumble into and come to rest in the bottom of the depressions 206. It is preferred that the depressions cover a relatively small percentage of the cross sectional area of the fluff layer 186, i.e., less than ten percent and preferably less than five percent. It will be appreciated that due to the resiliency of the fluff layer 186, the cross sectional area of each depression 206 will be less than the cross sectional area of each pick 202. In other words, depressions 206 tend to close somewhat after the picks 202 are removed.

Figure 23:
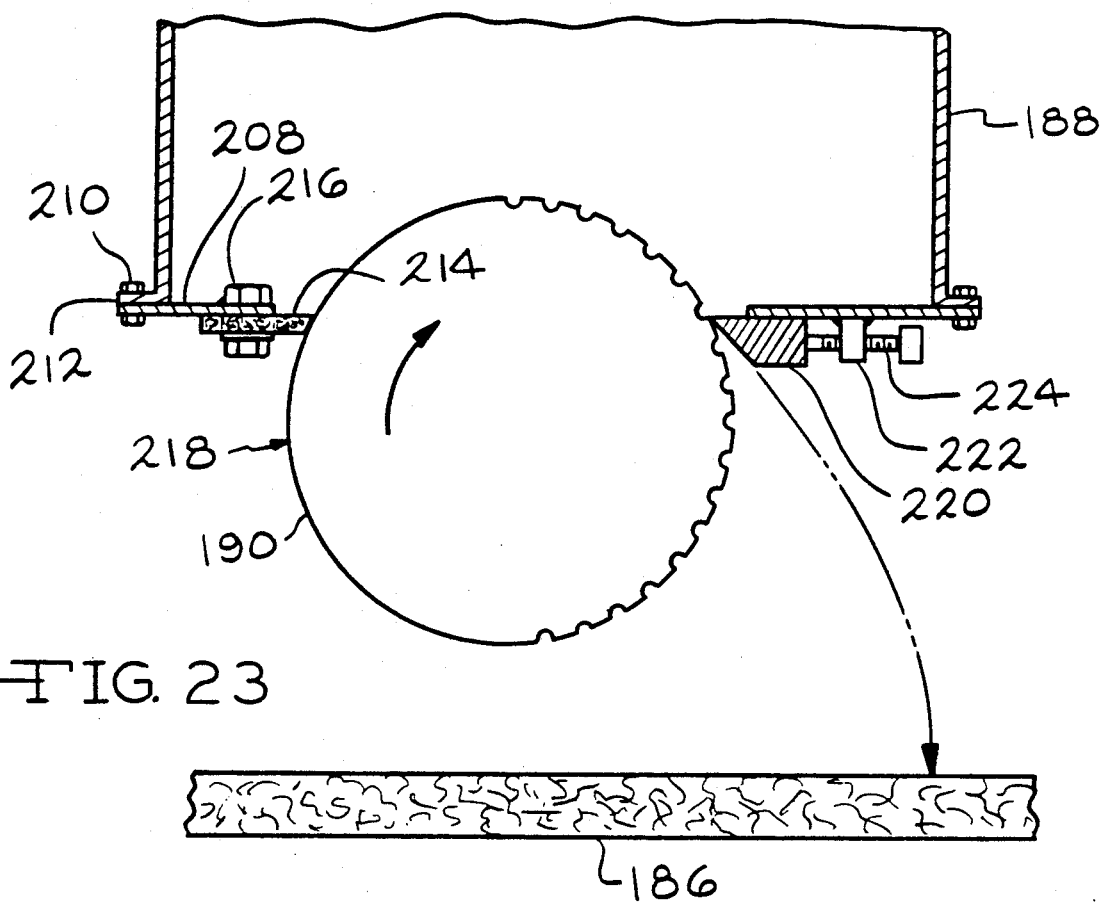
FIG. 23 is a side elevational view of dosing means and associated apparatus used in a process for depositing superabsorbent polymer in a given concentration in a target area in a layer of fluff and in a concentration less than the given concentration in areas adjacent to the target area.

Referring now to FIG. 23, an upper, minor portion of the dosing cylinder 190 is positioned within the hopper 188 and a lower, major portion of the cylinder is outside of the hopper 188. The bottom of the hopper 188 is covered in part by a plate 208 which is secured by fasteners 210 to a flange 212 provided at the bottom of the hopper 188. A rear dosing cylinder seal 214 is secured to the plate 208 by fasteners 216. Preferably, the seal 214 is composed of a material which exhibits low wear and high resilience. Felt and brass are two good candidate materials for the seal 214. An edge of the seal 214 engages an outer, discontinuous cylindrical surface 218 of the dosing cylinder 190 in dynamic sealing relationship to prevent superabsorbent polymer powder from passing out of the hopper between the plate 208 and the cylindrical surface 218 adjacent to the seal 214.

Opposite the seal 214, a doctor blade 220 is adjustably mounted on supports 222 which, in turn are secured to the plate 208. Threaded adjusters 224 allow for adjustment of the doctor blade position towards and away from the outer cylindrical surface 218 of the dosing cylinder 190. It is preferred to have a portion of the doctor blade 220 positioned immediately adjacent to the outer cylindrical surface 218 of the dosing cylinder 190 and spaced slightly therefrom so that powder can be dispensed from the hopper 188 between the doctor blade 220 and the dosing cylinder 190. A face 225 of the doctor blade 220 is angled and is oriented so that it extends downwardly and away from the outer cylindrical surface so that, as suggested by the arrow extending from the doctor blade 220, polymer powder is directed downwardly and away from the dosing cylinder 190 and onto the fluff 186.

Figure 24:
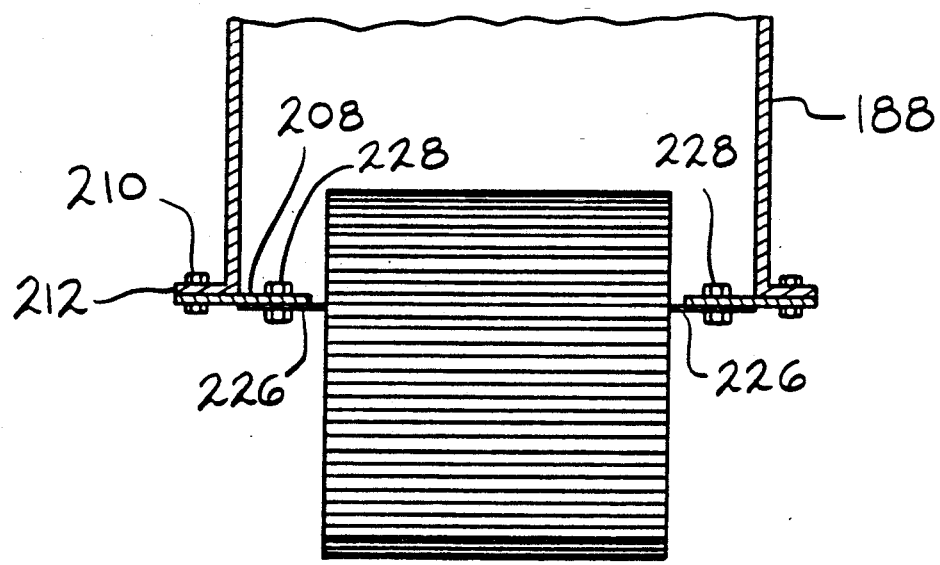
FIG. 24 is a front elevational view of the dosing means and associated apparatus shown in FIG. 23.
Figure 25:
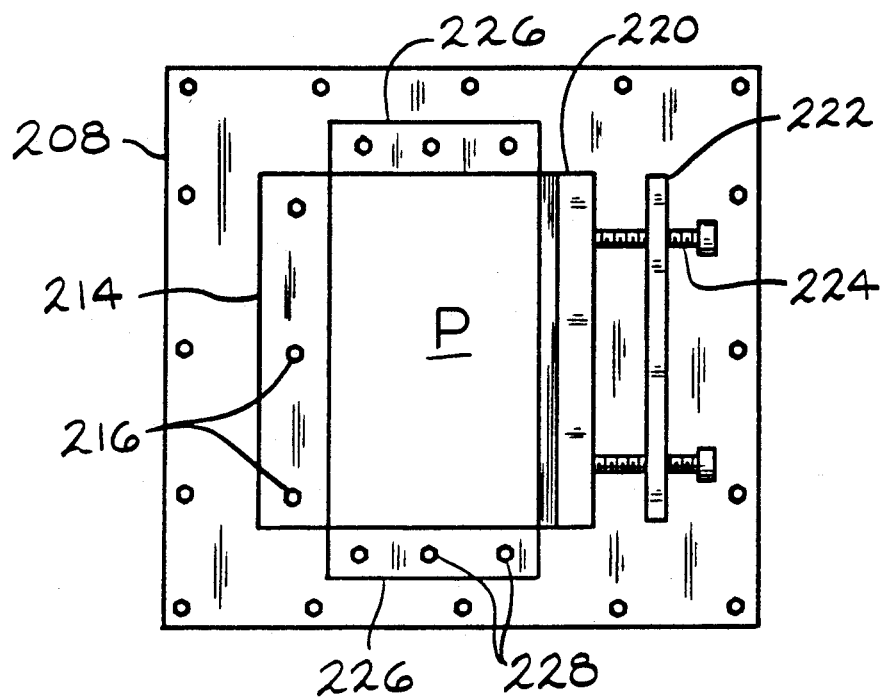
FIG. 25 is a bottom elevational view of confinements means which are used in conjunction with the dosing means shown in FIGS. 21, 23 and 24.

As shown in FIG. 24, side seals are provided between the plate 208 and the end plates 192 in the form of sealing flanges 226 secured by fasteners 228 to the plate 208. The sealing flanges 226, the seal 214 and the doctor blade 220 are shown in FIG. 25 as defining an opening in the shape of a polygon P, specifically, a rectangle. When the plate 208 is secured to the bottom of the hopper 188, the opening P constitutes a discharge opening for the hopper 188. The size of the discharge opening P is adjustable in as much as the distance between the seal 214 and the doctor blade 220 is freely adjustable by means of the threaded adjusters 224. Adjustment may also be provided in known fashion for the side sealing flanges 226. Thus, the plate 208 with the various seals can accommodate a plurality of dosing cylinders 190 of different diameters. The plate is also adapted to accommodate a dosing cylinder of a given diameter positioned so that more or less of the dosing cylinder extends into the hopper 188. It is preferred that the dosing cylinder be mounted so that approximately one fourth to one third of the cylindrical surface 218 is disposed inside of the hopper 188. It is essential, in any event, that the dosing cylinder 190 be positioned relative to the discharge opening P in the plate 208 so that the latter is effectively closed by the former at least one three sides so that discharge of material is effected only through designated dosing depressions in the cylindrical surface 218 and, if desired, between the cylindrical surface 218 and the doctor blade 220. The concentration of polymer powder deposited in a given location on a fluff layer is controlled by controlling the size and arrangement of dosing depressions formed in the cylindrical surface 218 of the dosing cylinder 190 and the distance, if any, between the doctor blade and the cylindrical surface 218.

Figure 26:
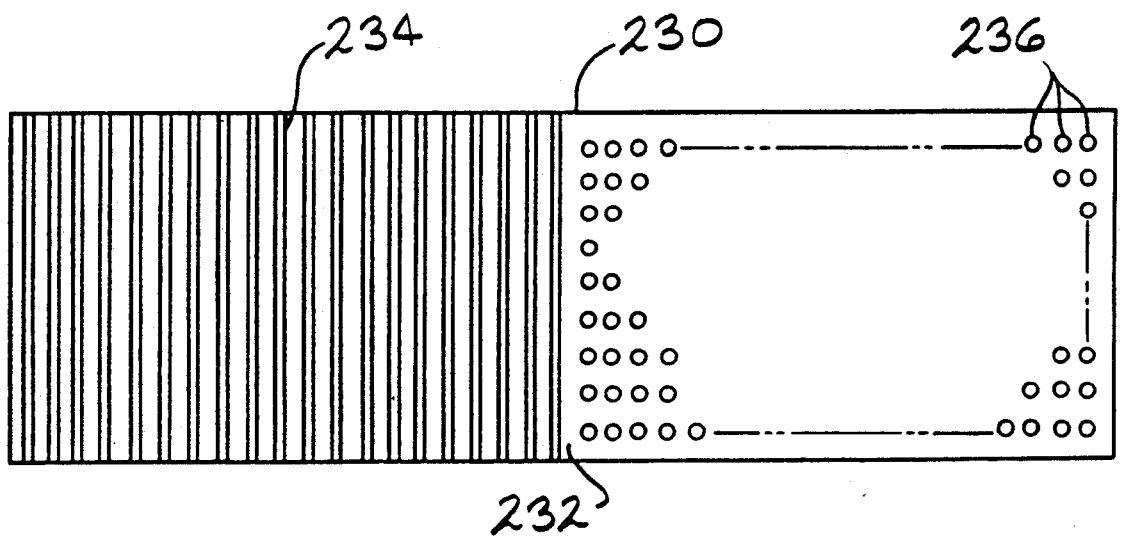
FIG. 26 is an elevational view of a surface which is suitable for use as the outer cylindrical surface of dosing means according to the present invention.

A pattern of dosing depressions which is useful in practicing the instant invention is shown in FIG. 26. A dosing cylinder 230 is illustrated as having been flattened out with an outer cylindrical surface 232 exposed. The surface 232 is interrupted by a plurality of sets of dosing depressions comprising first dosing depressions 234 and second dosing depressions 236. First dosing depressions 234 are defined by grooves in the surface 232 and second dosing depressions are defined by dimples 236 in the surface 232.

In producing absorbent articles comprising superabsorbent polymer powder deposited onto and into a fluff layer, it is preferred in accordance with one embodiment of the invention to provide a first, relatively high concentration of powder in a target area where maximum absorbency is needed and a second, relatively low concentration of polymer in areas adjacent to the target area.

As noted above, the dosing cylinder 190 is mounted for rotation about a horizontal axis on the shaft 194 which extends from drive means 196. It is desirable to have rotate the cylinder 190 at a constant rate which is proportional to the rate at which the fluff layer 186 is conveyed. In the case where the dosing means are associated with a diaper machine which includes a main drive line, it is preferred to drive the shaft 194 from the main drive line through the drive means 196. Alternatively, the dosing cylinder 190 can be driven independently of the machine which it serves. However the dosing cylinder is driven, it will be appreciated that the diameter/circumference of the cylinder and the relative rates at which the cylinder is rotated and the fluff is conveyed will determine the size or extent of the first and second areas. The size of the first area relative to the second area is determined, of course, by the relative sizes of the areas containing the first dosing depressions 234 and second dosing depressions 236.

A set up will now be described for producing an absorbent insert with a first target area having a given concentration of super absorbent polymer and adjacent areas having a second concentration of approximately one half of the given concentration. A dosing cylinder with a diameter of 8 and one half inches was mounted on shaft 194. Rows of first depressions 234 (FIG. 26) were machined into the outer cylindrical surface 218 of a the dosing cylinder. The depressions 234 were formed with an end mill having a three sixteenths nominal diameter and the depth of the depressions was maintained at thirty five thousandths of an inch. Each groove extended from one side of the dosing cylinder to the other and the width of the cylinder was 6 inches. The grooves were evenly spaced on one half inch centers around approximately half of the circumference of the cylinder and there were a total of twenty seven grooves.

Rows of second depressions 236 (FIG. 26) were machined into the cylinder and each row included 11 dimples spaced on one half inch centers. The rows of dimples were in turn spaced on one half inch centers and there were 26 rows covering approximately half of the periphery of the cylinder. The dimples were formed with a drill having a one quarter inch nominal diameter and the depth of the drilling was fifty one thousandths of an inch.

Absorbent inserts were produced with the dosing cylinder described above and the polymer used was ARIDALL 1125 which is available from Chemdal, Inc. The polymer has a density when dry of approximately 0.55 grams per cubic centimeter. Each dimple was designed to hold approximately 0.0075 grams of polymer and each groove was designed to hold approximately 0.1925 grams of polymer powder. The dosing cylinder was rotated once every time twenty nine and one eighth inches of fluff passed under it and the circumference of the cylinder was just under 27 inches. The doctor blade 220 was spaced slightly from the cylindrical surface 218 so that approximately 0.260 grams of polymer would pass between the blade 220 and the cylinder 190 if it had a smooth surface, per inch of circumference of the cylinder 190, so that approximately 7 grams of polymer powder would be deposited evenly over the twenty nine and one eighth inch long fluff section. This steady or even deposition of polymer powder was complemented by the deposition of a first, relatively high concentration of polymer powder from the grooves in a first area on the fluff layer and the deposition of a second, relatively low concentration of polymer powder from the dimples in a second area. The first and second areas alternated and approximately 14.2 grams of polymer powder was deposited over each twenty nine and one eighth inch section of fluff. This was slightly more polymer powder than was desired, so the doctor blade 220 was advanced towards the cylinder 190, a slight amount, and additional absorbent inserts were produced. The apparatus was operated to produce fluff sections twenty nine and one eighth inches long wherein a central area having a length of 10.3 inches contained 6 grams of polymer and two adjacent areas having lengths of 9.4 inches located at each end of the fluff section contained 3 grams of polymer each.

Referring now to FIG. 27, a continuous fluff layer 240 has a plurality of alternating target areas 242 and longitudinally adjacent regions or areas 244. Superabsorbent polymer powder has been applied to the fluff layer 240 by apparatus including a doser wheel so that there is a first, relatively high concentration of superabsorbent polymer powder in the target area 242 and a second, relatively low concentration of superabsorbent polymer powder in the adjacent areas 244. The fluff layer 240 is produced to be cut into discreet lengths to produce absorbent inserts represented by dotted lines 246 defining the ends of the insert and dotted lines 248 defining leg cut outs. The absorbent inserts are suited for incorporation into a disposable diaper in accordance with any of the previously described embodiments wherein superabsorbent polymer is deposited on fluff. In the case of an absorbent insert for use in a disposable diaper, the position of the leg cut outs 248 and the ends of the absorbent inserts produced from the fluff layer 240, relative to the areas 242 and 244 of different polymer concentration, is critical and the target area 242 of high polymer powder concentration must be positioned between the leg cut outs 248. It is preferred that the area 242 of high polymer powder concentration extend from one third to one half of the length of a given absorbent insert and the remaining area(s) 244 of a low polymer concentration be positioned at each end of the high polymer powder concentration area 242.

It has been discovered that it is nigh impossible, on the basis of a visual inspection of a fluff layer having adjacent, alternating areas of different polymer powder concentrations, to determine where one area of polymer powder concentration ends and the next area of different polymer powder concentration begins. Accordingly, it is preferred that apparatus for depositing polymer on fluff in different concentrations include means for establishing an index mark from which it can be determined by visual inspection that the heavy polymer powder is in the correct location either in a finished product or in the absorbent insert containing the polymer powder.

One embodiment of a fluff layer including a visual indicator of the relative locations of areas having different concentrations of polymer powder is shown in FIG. 27. As discussed above, a fluff layer indicated at 240 has different concentrations of polymer in discreet areas. There is a first area 242 of high polymer powder concentration and a second area 244 of low polymer powder concentration centrally located in the fluff mat 240. As indicated by dotted lines 246, the fluff layer can be cut into discreet lengths in which there is centrally located a first area 242 of high polymer powder concentration and adjacent that, on each end, two second areas 244 of low polymer powder concentration. Dotted lines 248 indicate areas where leg cut outs may be positioned and they are located immediately adjacent to the first area 242 of high polymer powder concentration. A mark 250 is positioned on the fluff layer adjacent to one of the second areas 244 of low polymer powder concentration. The mark 250 may consist of ink applied to the fluff layer at the hopper 188 and dosing wheel 190 station shown in FIGS. 21 and 28. Alternatively, the mark may consist of any other visually perceptible indicia such as a hot melt adhesive or even an embossment. A printing wheel 252 may be provided directly on a shaft 254 on which the dosing cylinder 190 is mounted. A stamp 256 is mounted on the periphery of the printing wheel 252 and can be inked by conventional inking rollers (such as those described below in connection with a second embodiment of indexing apparatus) so that a mark is applied to the fluff at intervals corresponding with one or more revolutions of the dosing wheel so that the location of the mark gives a positive visual indication of the relative location of the first and second areas of polymer powder concentration. The mark 250 can be located anywhere on the fluff layer; it is only necessary to have the mark be consistently positioned in the same place relative to the location of the first and second areas of different polymer powder concentration. It may be desirable to position the mark 250 in a portion of the fluff layer 240 which will be trimmed from the fluff layer, for example, within the dotted lines 248 indicating leg cut-outs. This has the advantage of leaving no indexing mark on the finished product. Moreover, such a placement can make the mark serve as a quality control mechanism because, if there is slippage of the fluff layer between the doser wheel station and the die cutting station (not shown) where the leg cut outs are trimmed, the mark may be outside of the leg cut out region and it will be visible on the fluff pad that leaves the die cutting station, indicating that there has been slippage or some other cause for mis-indexing as between the dosing station and the die cutting station.

Another embodiment of indexing apparatus is indicated generally at 258 in FIG. 28. This embodiment does not require use of the printing wheel 252 although it can be used together with the apparatus constituting the embodiment described here. In apparatus according to this embodiment, there is associated with the dosing cylinder shaft 254 a proximity switch comprising a shaft sender 260 and a receiver 262 and it is operable to generate an electrical signal which is indicative of the rate at which the dosing cylinder 190 and the dosing cylinder shaft 254 are rotating. A signal from the proximity switch is fed via line 264 to a controller 266 which, together with the proximity switch, constitute a pulse generator for generating a signal which precisely reflects the rate at which the dosing wheel 190 is rotating. That signal, in turn, is fed through a line 268 to a variable speed direct current motor 270 at a station for printing a quality control mark on each absorbent product. The quality control station is downline from a non-woven cover feeding station where non-woven facing sheet material is fed from a roll 272 onto a substrate comprising discreet cut sections of fluff 274 on top of a continuous sheet of water impervious polymeric backing material 276. Stations which are intermediate the dosing station and the non-woven station are not illustrated because they are not part of this embodiment. Nonetheless, this embodiment has consequences for the intermediate stations because, as described below, it provides a positive check of whether or not these stations are operating synchronously.

When the doser wheel is operating, it is rotated once every time a given length of fluff is conveyed beneath it and the given length corresponds with the length of the discreet fluff sections 274 shown in FIG. 28. A personal absorbent article incorporating a fluff section 274 has a length, which is longer than the given length, and is the distance between dotted lines 278 which correspond with positions at which the substrate will be die cut into discreet individual absorbent articles. A printing wheel 280 is mounted on a shaft 282 which is driven by the motor 270. The printing wheel 280 has a circumference which is equal to the length of a personal absorbent article being produced. It is preferred that the shaft 282 be rotated by the motor 270 at the same rate at which the dosing cylinder is rotated so that the printing wheel rotates once every time the dosing cylinder rotates once. As a consequence, when the line including the apparatus shown in FIG. 28 is operating synchronously, a print head 284 on the print wheel 280 will imprint a mark 286 at precisely the same longitudinal location in each personal absorbent article and conversely, if the line gets out of synchronization, due to slippage of material, for example, the mark 286 will be imprinted at a different longitudinal location and operators will be alerted to the existence of a machine difficulty. The precise longitudinal location of the mark 286 can be determined when the machine is started and, again, so long as it operates correctly without material slippage, the mark will be imprinted in the same position on subsequently produced absorbent products.

Ink is supplied to the print head 284 through an inking roller 288 which rotates in an ink supply well 290 and an ink transfer roller 292. This inking arrangement can be provided in association with the print wheel 252 on the dosing cylinder shaft 254 which is described above. The print wheel 280 may be driven through a power take off from the line on which the apparatus 258 is provided, in lieu of the motor 270.

The foregoing description is intended to enable those skilled in the art to practice the present invention and constitutes the best mode presently known for practicing the invention.

Undoubtedly, modifications will occur to those skilled in the art, and such modifications may be resorted to without departing from the spirit and scope of the invention disclosed herein and claimed below.

1. Apparatus for depositing particulate material on a moving substrate, in at least two different concentrations in discreet portions of said substrate, said apparatus comprising, in combination, a horizontal conveyor for supporting the substrate and conveying the substrate at a substantially constant rate of speed, a material hopper for holding the particulate material, said hopper being positioned above said conveyor, means defining a discharge opening in the lower end of said hopper, dosing means positioned in the hopper discharge opening, said dosing means comprising an outer, discontinuous, cylindrical surface and opposed end plates which, together, abut said means defining said discharge opening, thereby preventing the passage of particulate material between said means defining the discharge opening, on the one hand, and the cylindrical surface and the end plates on the other hand, drive means for rotating said cylindrical surface of said dosing means about a horizontal axis at a substantially constant rate of rotation, said horizontal axis being positioned relative to said discharge opening so that, at any given angle of rotation of the cylindrical surface, a portion of the cylindrical surface is inside said material hopper and the remaining portion of the cylindrical surface is not inside said material hopper, means defining a first set of dosing depressions in a first portion of said outer cylindrical surface, said first set of dosing depressions having a given volume per unit of cylindrical surface area and means defining a second set of dosing depressions in a second portion of said cylindrical surface, said second set of dosing depressions having a volume per unit of cylindrical surface area which is less than the given volume per unit of cylindrical surface area and greater than zero, so that, when the cylindrical surface is rotated at a constant rate, particulate material is withdrawn from the hopper and deposited on different portions of the substrate in at least two different concentrations every time the cylindrical surface revolves.

2. Apparatus as claimed in claim 1 which additionally includes indexing means for making a visually perceptible mark on the substrate or an article incorporating wherein said mark provides a readily discernable indication of the location of the discreet portions of said substrate having the two different concentrations of particulate material.

3. Apparatus as claimed in claim 1 which additionally includes picker means for producing a plurality of depressions extending a substantial distance into the substrate for receiving a relatively small percentage of the particulate material deposited thereon.

4. The apparatus claimed in claim 1 wherein said first and second portions of said outer cylindrical surface, together, constitute substantially all of said cylindrical surface.

5. Apparatus for depositing particulate material on a moving substrate, in at least two different concentrations in discreet portions of said substrate, said apparatus comprising, in combination, a horizontal conveyor for supporting the substrate and conveying the substrate at a substantially constant rate of speed, a material hopper for holding the particulate material, said hopper being positioned above said conveyor, means defining a discharge opening in the lower end of said hopper, dosing means positioned in the hopper discharge opening, said dosing means comprising an outer, discontinuous, cylindrical surface and opposed end plates which, together, abut said means defining said discharge opening, thereby preventing the passage of particulate material between said means defining the discharge opening, on the one hand, and the cylindrical surface and the end plates on the other hand, drive means for rotating said cylindrical surface of said dosing means about a horizontal axis at a substantially constant rate of rotation, said horizontal axis being positioned relative to said discharge opening so that, at any given angle of rotation of the cylindrical surface, a portion of the cylindrical surface is inside said material hopper and the remaining portion of the cylindrical surface is not inside said material hopper, means defining a first set of dosing depressions in a first portion of said outer cylindrical surface, said first set of dosing depressions having a given volume per unit of cylindrical surface area, means defining a second set of dosing depressions in a second portion of said cylindrical surface, said second set of dosing depressions having a volume per unit of cylindrical surface area which is less than the given volume per unit of cylindrical surface area and greater than zero and doctor blade means supported on said hopper adjacent to said cylindrical surface but spaced, slightly apart therefrom so that, if the cylindrical surface was smooth, particulate material could pass out of the material hopper between the doctor blade means and the cylinder surface, wherein, when the cylindrical surface is rotated at a constant rate, particulate material is withdrawn from the hopper and deposited on different portions of the substrate.

6. Apparatus as claimed in claim 5 which additionally includes indexing means for making a visually perceptible mark on the substrate or an article incorporating wherein said mark provides a readily discernable indication of the location of the discreet portions of said substrate having the two different concentrations of particulate material.

7. Apparatus as claimed in claim 5 which additionally includes picker means for producing a plurality of depressions extending a substantial distance into the substrate for receiving a relatively small percentage of the particulate material deposited thereon.

8. The apparatus claimed in claim 5 wherein said first and second portions of said outer cylindrical surface, together, constitute substantially all of said cylindrical surface.

* * * * *

UNITED STATES PATENT AND TRADEMARK OFFICE
CERTIFICATE OF CORRECTION

PATENT NO. : 5,072,687

DATED : Dec. 17, 1991

INVENTOR(S) : Winalee G. Mitchell et al

It is certified that error appears in the above-identified patent and that said Letters Patent is hereby corrected as shown below:

Title page, item [54] and col. 1, line 1, delete title and replace with
--APPARATUS FOR DEPOSITING PARTICULATE MATERIAL AND FOR PRODUCING
ABSORBENT PRODUCTS--.

Signed and Sealed this

First Day of June, 1993

Attest:

MICHAEL K. KIRK

Attesting Officer

Acting Commissioner of Patents and Trademarks